US011493514B2

(12) United States Patent
Al Ahmad et al.

(10) Patent No.: US 11,493,514 B2
(45) Date of Patent: Nov. 8, 2022

(54) METHOD AND SYSTEM FOR VIRUS AND PROTEIN-ANTIBODY INTERACTIONS DETECTION AND MONITORING BASED ON OPTICAL LIGHT INTENSITY AND ELECTRICAL PARAMETERS

(71) Applicant: United Arab Emirates University, Al Ain (AE)

(72) Inventors: Mahmoud F. Y. Al Ahmad, Al Ain (AE); Tahir A. Rizvi, Al Ain (AE); Farah Mustafa, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 17/379,496

(22) Filed: Jul. 19, 2021

(65) Prior Publication Data

US 2022/0018839 A1 Jan. 20, 2022

Related U.S. Application Data

(60) Provisional application No. 63/054,022, filed on Jul. 20, 2020.

(51) Int. Cl.

*G01N 33/569* (2006.01)
*G01N 21/47* (2006.01)
*G01N 15/14* (2006.01)

(52) U.S. Cl.

CPC ....... *G01N 33/56983* (2013.01); *G01N 21/47* (2013.01); *G01N 2015/1477* (2013.01); *G01N 2333/165* (2013.01)

(58) Field of Classification Search

None
See application file for complete search history.

(56) References Cited

U.S. PATENT DOCUMENTS

2004/0258571 A1* 12/2004 Lee ....................... B01L 3/5027 436/86
2005/0112559 A1* 5/2005 Leung .................. C07K 14/005 435/5

(Continued)

FOREIGN PATENT DOCUMENTS

WO 2011060184 A1 5/2011
WO 2015116083 A1 8/2015
WO 2021081476 A1 4/2021

OTHER PUBLICATIONS

Mavrikou et al. (Sensors. May 2020; 20: 3121).*

(Continued)

*Primary Examiner* — Shanon A. Foley
(74) *Attorney, Agent, or Firm* — Boyle Fredrickson, S.C.

(57) ABSTRACT

A novel method of detecting and destroying viral transmissions such as SARS-CoV-2 transmission is described. The proposed technique uses a light source such as that from a smart phone and a mobile spectrophotometer to enable detection of proteins in solution. The technique allows for detecting soluble preparations of for example spike protein subunits from SARS-CoV-2, followed by detection of the actual binding potential of the spike protein with its host receptor, for example the angiotensin-converting enzyme 2 (ACE2) or other antigens or elements. The results are validated by showing that this method can detect antigen-antibody binding using two independent protein-antibody pairs. Finally, this technique is combined with DC bias to show that introduction of a current in the system can be used to disrupt the antigen-antibody reaction, suggesting that this technique can be a powerful means of disrupting virus transmission by destroying virus-receptor interactions.

26 Claims, 13 Drawing Sheets
(13 of 13 Drawing Sheet(s) Filed in Color)

(56) References Cited

U.S. PATENT DOCUMENTS

| | | | | |
|---|---|---|---|---|
| 2010/0112547 | A1* | 5/2010 | Lu | C07K 5/1019 435/5 |
| 2014/0255916 | A1 | 9/2014 | Sigal | |
| 2014/0320849 | A1* | 10/2014 | Chou | B03C 5/026 356/72 |
| 2015/0203925 | A1 | 7/2015 | Israel et al. | |
| 2017/0234801 | A1 | 8/2017 | Unlu et al. | |
| 2017/0362668 | A1 | 12/2017 | Glezer et al. | |
| 2021/0123883 | A1 | 4/2021 | Tabib-Azar | |

OTHER PUBLICATIONS

Bakr Ahmed Taha, Yousif Al Mashhadany, Mohd Hadri Hafiz, Mokhtar, Mohd Saiful Dzulkefly Bin Zan, and Norhana Arsad; An Analysis Review of Detection Coronavirus Disease 2019 (COVID-19) Based on Biosensor Application; Sensors; 2020; 29 pages.

Aaron T. Fafarman et al., Quantitative, directional measurement of electric field heterogeneity in the active site of ketosteroid isomaerase, Proceedings of the National Academy of Sciences, Feb. 7, 2012, 11 pages, vol. 109, No. 6.

Mahmoud Al Ahmad et al., Development of an Optical Assay to Detect SARS-CoV-2 Spike Protein Binding Interactions with ACE2 and Disruption of these Interactions Using Electric Current, Nov. 28, 2020, 21 pages.

Jun Lan et al., Structure of the SARS-CoV-2 spike receptor-binding domain bound to the ACE2 receptor, Nature, May 14, 2020, 16 pages, vol. 581.

Xiuyuan Ou et al., Characterization of spike glycoprotein of SARS-CoV-2 on virus entry and its immune cross-reactivity with SARS-CoV, Nature Communications, 2020, 12 pages.

Marc C. Johnson et al., Optimized Pseudotyping Conditions for the SARS-COV-2 Spike Glycoprotein,Journal of Virology, Nov. 2020, 10 pages, vol. 94, Issue 21.

International Search Report for Application No. PCT/IB2021/056520, dated Sep. 23, 2021, 6 pages.

Written Opinion for Application No. PCT/IB2021/056520, dated Sep. 23, 2021, 8 pages.

* cited by examiner (a)

(b)

(a)

(b)

METHOD AND SYSTEM FOR VIRUS AND PROTEIN-ANTIBODY INTERACTIONS DETECTION AND MONITORING BASED ON OPTICAL LIGHT INTENSITY AND ELECTRICAL PARAMETERS

CROSS-REFERENCE TO RELATED APPLICATION

This application is a U.S. Non-Provisional Patent Application that claims priority to U.S. Provisional Patent Application No. 63/054,022, filed on Jul. 20, 2020 and entitled "Method and System for Virus and Protein-Antibody Interactions Detection and Monitoring Based on Optical Light Intensity and Electrical Parameters", the entirety of which is hereby incorporated by reference.

FIELD OF THE INVENTION

The present disclosure relates in general to a method and system for virus detection and monitoring, and more specifically to a method and system for virus and protein-antibody interactions detection and monitoring based on optical light intensity and electrical parameters.

BACKGROUND

In late December 2019, patients with an atypical pneumonia due to a novel coronavirus were reported in Wuhan, China. Since then, the novel coronavirus disease 2019 (COVID-19) has become a pandemic that has spread worldwide to virtually every country. This pandemic has caused massive social and economic disruptions in nearly every country and therefore global research and development efforts are being geared towards development of vaccines and therapeutics for the prevention and treatment of COVID-19, in order to normalize the situation.

Unfortunately, the complete clinical picture of COVID-19 is not yet fully known and most likely depends upon a number of factors, including virus characteristics. As of Jul. 7, 2020, more than 11,645,109 cases of COVID-19 infection had been confirmed worldwide with 538,780 deaths, revealing a case fatality rate (CFR) of 4.6%. Successful detection of SARS coronavirus 2 (SARS-CoV-2) plays an important role in stopping the spread.

The novel severe acute respiratory syndrome coronavirus 2 (SARS-CoV-2) that causes COVID-19 enters the susceptible cells primarily via endocytosis using its spike (S) protein (3-5). The viral S protein is a homotrimer that protrudes from the virion surface (6) and is responsible for entry into susceptible cells by binding to the human angiotensin converting enzyme 2 (ACE2) protein (3-5). Once internalized, the virus starts to replicate within the cell (7). The nucleocapsid (N) protein of SARS-CoV-2, is the largest structural protein of the virus which coats its large genomic RNA and is responsible for creating its helical structure (8). Compared to the viral S protein, the N protein is much more conserved (~90%), is expressed at high levels during infection, and is highly immunogenic (8). This is for example described in the publication Y. Cong, M. Ulasli, H. Schepers, M. Mauthe, P. V'kovski, F. Kriegenburg, V. Thiel, C. A. M. de Haan, F. Reggiori, *Nucleocapsid Protein Recruitment to Replication-Transcription Complexes Plays a Crucial Role in Coronaviral Life Cycle. J. Virol.* 94 (2019), doi:10.1128/JVI.01925-19.

Currently, oropharyngeal and nasopharyngeal swabs are primarily used for virus detection. However, it is not clear how many virus particles of SARS-CoV-2 are needed to trigger an infection. It has been anticipated that the corresponding dose to establish an infection in exposed people could be as little as 10 virus particles. Other studies suggest a relatively higher dose, ranging from a few hundred to thousands of particles. It has been estimated that SARS-CoV-2 exhibits a higher rate of virus replication compared to SARS-CoV-1 which can increase disease severity. Statistically, confirmed COVID-19 cases worldwide are 100 times higher than the confirmed cases of SARS and MERS. This is because, 1) SARS-CoV-2 replicates to much higher levels in the nose and mouth than SARS and MERS, and 2) this leads to very high levels of virus shedding in the environment by people who are either pre-symptomatic or asymptomatic. Thus, a huge percentage of infected people can transmit the virus without realizing that they are even infected.

Rapid detection methods independent of lab setting have been identified as one of the foremost priorities for promoting epidemic prevention and control. Currently, there are two main strategies for the detection of COVID-19. The first is a real time reverse transcriptase (RT) polymerase chain reaction (RT PCR)-based strategy that detects the viral nucleic acid in patient samples (presence of the viral RNA). The second strategy is an immunological assay that detects viral protein antigens or serum antibodies produced as a result of the body's immune response to the viral infection. The two strategies complement each other, with the qPCR strategy detecting the virus during its active phase, while the immunological assay identifies individuals who have developed antibodies to fight the disease. An interesting approach to COVID-19 diagnosis that utilizes either of these strategies, is by the use of biosensors (12, 13). Biosensors interact with biomolecules and transduce their readings into measurable outputs, such as optical, electrical and enzymatic. Biosensors can provide label-free, real-time detection and curtailment of non-specific binding. However, they also face the challenge of efficient immobilization of biomolecules on the sensing surface (14).

Currently, the molecular technique of quantitative real time polymerase chain reaction (qRT PCR) is the gold standard for SARS-CoV-2 detection using samples from respiratory secretions. However, it is a time consuming and cumbersome procedure that takes long processing times over days for results. Several other molecular assays have been developed to detect SARS-CoV-2, such as enzyme-based assays like ELISAs, and rapid tests that aim to detect either antibodies against the virus or the viral antigen themselves. Nevertheless, most of these antigen-antibody-based assays have failed quality control due to their rapid development without proper testing and result in either false negative or false positive detection due to the long time it takes to develop serum responses to the viral infection (from days to two weeks).

Recent reports have found distinctive UV-visible light spectra in the range of 250-800 nm for proteins rich in charged amino acids, are in monomeric form, and devoid of aromatic amino acids (15-19). Prasad et al. have shown that the protein charge transfer spectra (ProCharTS) band comprises of facile photoinduced peptide backbone to side chain charge transfer and side chain to side chain charge transfer transitions in charged amino acids such as lysine (Lys) and glutamate (Glu) (18). In fact, all naturally occurring charged amino acids can be identified as either electron donor (D), bridge (B), or electron acceptor (A) units. Within protein folds, the charged side chains of these amino acids (e.g., Lys amino or Glu carboxyl groups), and the peptide backbone play the role of D and A groups, while the aliphatic (non-polar) part of the side chain or the intervening protein/solvent medium forms the B component of the D-B-A units. While CT transitions for charged amino acid monomers are expected to be in the deep UV (below 250 nm), strong inter-residue electronic couplings imposed by protein folds can shift such transitions dramatically to the visible end. Previous molecular dynamics (MD) and electronic structure analysis revealed three specific factors which primarily determine the ProCharTS absorption range: (1) distance between the side chains of charged amino acids (which could be in the range of 2-10 A or more), (2) the charge complementarity of the interacting side chains and (3) the medium pH (19). Solvation and conformations of the amino acid side chains and the peptide backbone were also shown to modulate the spectral range of the CT transitions to a lesser extent (18).

Electrostatic analysis has been used in related art to study protein interactions at a structural level. For example, it was observed that the protein surface of ACE2 shows negative electrostatic potential, while the S proteins of the SARS-CoV/SARS-CoV-2 exhibit positive potential (20). Additionally, it was found that SARS-CoV-2 S protein is slightly more positively charged than that of SARS-CoV, giving it a higher affinity to bind to negatively charged regions of the ACE2 (30% higher binding energy (7)). Similarly, the SARS-CoV-2 N protein has three distinct but highly conserved parts: the N-terminal RNA-binding domain (NTD) which is responsible for RNA binding via its distinct basic (positively charged) finger and palm regions: a C-terminal dimerization domain (CTD) which is responsible for oligomerization, and intrinsically disordered central Ser/Arg (SR)-rich linker which is responsible for linker for primary phosphorylation, respectively (21).

Thus, most of the methods used so far either require skilled manpower and are time consuming if accurate, or not reliable at all, if fast. On the other hand, biosensor technology provides excellent sensitivity, but requires metal coating deposited on the device, thereby raising cost. Furthermore, some of these biosensors suffer from temperature-dependence which can be a hindrance for portable biosensors in outdoor conditions. Some require expensive reagents and reaction times are often longer.

RELATED ART

Examples of related art with different assay methods and analysing techniques are found in various publications. For example, the patent publication US2017362668A1 to Meso Scale Technologies with the title Co-binder assisted assay methods disclose methods for reducing cross-reactivity between species employed in multiplexed immunoassays.

Another example of related art is found in the patent publication US2021123883A1 to University of Utah Research Foundation with the title Whole virus quantum mechanical tunneling current and electronic sensors. This publication discloses a field effect transistor (FET) biosensor for virus detection of a selected virus within a sample volume.

A further example of related is the patent publication WO2021081476A1 to University of Utah Research Foundation with the title Zero Power visible colorimetric pathogen sensors. This piece of related art shows a method in which a visibly perceived colorimetric pathogen sensor comprises a substrate and a molecular recognition group coupled to the substrate. The molecular recognition group can bind a target pathogen and when that occurs, the reflected light cab be altered thereby changing apparent color, thus indicating the detected target pathogen.

The article with the title An Analysis Review of Detection Coronavirus Disease 2019 (COVID-19) Based on Biosensor Application by Bakr Ahmed Taha et al. summarized technologies for the detection of coronavirus disease 2019 (COVID-19) technologies with biosensors that operate using laser detection technology.

The related art patent publication WO2011060184 to Cermed Corporation with the title Cervical cancer screening by molecular detection of human papillomavirus-induced neoplasia further shows point-of-care tools for screening biological samples for markers associated with pathogenic microbial infections. This publication discloses a technology for screening cervical cells for the expression of proteins that occur because of human papillomavirus infection and progression to invasive cervical cancer.

Another related art patent publication WO2015116083 to Hewlett Packard Development with the title Microfluidic sensing device. This publication discloses a microfluidic sensing device that comprises a channel and an impedance sensor within the channel. A particle in a fluid passing the sensor is identified based on the sensed impedance characteristics.

There is a need in the field for fast, cheap and accurate methods of detection of a virus such as SARS-CoV-2, which may be used to slow the spread of the virus till a vaccine or effective therapy can be found.

SUMMARY OF THE INVENTION

The present disclosure describes embodiments for a method and system for virus detection and monitoring.

The current disclosure describes embodiments from several aspects. Some aspects describe a system and method to detect and monitor the possible binding or interactions between proteins and proteins, proteins and antibody, viruses and proteins, viruses and antibodies, cells and proteins, cells and antibodies as well as virus-cell, or cell-cell interactions, or any interactions between any part of protein, antibody, virus, cell with any part of protein, antibody, virus, cell of the same or different kind. Embodiments are based on and utilize the higher positive electrostatic potential of SARS-CoV-2 N protein and its antibody for an opto-electrical detection method and system to successfully detect virus infection in nasal swabs from SARS-CoV-2-infected individuals.

System embodiments incorporate a source capable of emitting light, natural or manmade. The emitted light spectrum can cover the whole spectrum. This light passes through a sample, and its absorbance, reflectance, transmittance or any other type of scattering, corresponding intensities or any other possible forms that could be extracted out of these intensities and can be collected using a spectrometer or any light-based detector, sensor or device. These intensities are measured and recorded over a time-period or can be mapped to the time domain in order to determine, measure or study light scattering parameters.

Embodiments comprise a transparent container allowing light to pass through the material without appreciable scattering of light configured for holding a sample. The sample under test can be loaded into the transparent container, which in different variants is any type of plate, box, tube, or any type of paper made out of transparent material or any other material, allowing light to pass through the material without appreciable scattering of light. The sample or specimen can either be tested in place or can be taken out to be tested away from its origin.

The light-based source, the light-based detector and the sample is in different embodiments aligned with each other for example in a straight line (i.e., source-sample-detector) or any other possible alignment that enables the measurement of the mentioned intensities.

During the measurement, the sample can be added to the appropriate container, applying the measurement conditions, collecting the responses, either directly measured intensities are collected and/or direct relationship with time is established or the direct measured data are further processed to extract parameters or set of parameters and correlate them with time to establish the relationship.

This relationship is further considered to determine the type of interaction either by direct judgment or further processing. A mathematical relation can be constructed to represent the interaction process. For example, if within the time-period, this relationship shows nonlinearity, then this means that the interaction took place; if it shows a constant behaviour, then the interaction did not take place. In case of linear relationship that can be represented with a slope, the two kinds of elements or more than two elements under investigation, their individual intensities should be measured and considered accordingly.

The proposed method can monitor vaccine or drug development process.

Different embodiments comprise any type of equipment that can measure light intensity is also included. For example, a camera or any possible image-based system that can take either video or pictures or that has the ability to map light intensities to any possible form, or its output can be processed further. Embodiments are configured to utilize the phenomenon that when two proteins bind or a molecular interaction takes place between them, due to this interaction, a possible form of kinetic energy is produced, for example as a cloud. This kinetic energy can cause disturbances, such as altering the Brownian motion of the molecules that can change or alter light distribution on the surface of the sample or inside. The generation of a cloud-like response due to the biochemical interaction would also disturb the light intensity distribution and accordingly the measured light intensities.

Further embodiments use techniques and equipment for conducting chronoamperometry or chronopotentiometry measurements or other measurements based on this principle to detect and monitor such interactions/binding. The measured value, either current or voltage over time, are used in different embodiments to explore the interaction. When an interaction occurs, the measured profile over time will increase or decrease in trend, depending upon the nature of the test samples, resulting in either an exponential growth or a decay behaviour. Furthermore, in other embodiments current voltage or capacitance voltage, impedance, or any other possible electrical-based measurements are used for this purpose.

Low and high frequency, optical and/or electrical scattering parameters or propagating waves, or any other possible form of measurements are used in yet other embodiments.

The linear electro-optic effect is the change in the index of refraction that is proportional to the magnitude of an externally applied electric field. The electro-optic effect may also be non-linear, for example over a wider range. Hence, the measured light intensity varies with DC electric voltage. The DC bias will also change the current and capacitance as they depend on the applied voltage. Values for the capacitance can for example be extracted from scattering parameters or impedance measurements or from determined relations between the parameters. This relationship/dependency can be converted to a chart or be expressed as a relationship that could be used for detection enhancement and further identification of the sample under test. For a specific virus type, the corresponding capacitance and light intensity at zero bias could also be used for further detection purposes. In embodiments, the voltage dependency is used to provide more information, for example about the viral load and to identify the viral stage infection.

In embodiments sample strips are provided to collect a sample of analytes from a test object such as a patient, a fluid or a physical object, or to store a sample of analytes collected from such test objects e.g., for later analysis. Sample strips are in embodiments configured with a portion coated with antibodies. Such sample strips coated with antibodies are preferably designed as flexible strips and are preferably kept inside packs with probe medium for granting their lifetime and functionality. These sample strips are in embodiments configured to be used directly loading a sample from a nasal swab or some other probe. In other embodiments the sample strip is configured to be formed and attached to a probe to be inserted inside the nose. In embodiments, such sample strips may also be coated with a probe electrode to conduct current measurements.

Embodiments comprises a device for nasal sampling configured to be insertable inside the nose of a human test object. Some of these embodiments are configured such that a sample strip is attachable at the end of an elongate section of the device. The sample strip is attached to touch the nasal walls when the nasal sampling device is inserted into the nose. Embodiments of this sampling device is probed with or comprises two electrodes configured to apply current over time continuously through a chip integrated within it, such that an electric field is applied over a sample of analytes collected on the sample strip. In embodiments, an integrated light source and detector are incorporated in the sampling device and configured to expose the sample to light and to detect light passing through the sample, enabling the capability to conduct light intensity measurements non-invasively.

The concept of strips can be further used to detect different samples or specimens taken from blood, breath, urine, nasal swabs, stool, etc. For example, the subject can breathe, exhale, or sniff into a device such as embodiments configured with a probe coated with antibodies. If binding occurs, the integrated device should be able to pick up the interaction, confirming that the patient is infected with the virus to which the antibodies are directed against.

An example of embodiments for the use of the technologies specified herein is provided for SARS-CoV-2 diagnosis, though depending upon the antibody used, it is in other embodiments configured for the detection of any respiratory virus such as influenza, respiratory syncytial virus (RSV), adenoviruses, or other coronaviruses like SARS and MERS. The antibody against the virus in question is in embodiments be coated on flexible sample strips for increasing their lifetime and functionality and kept inside packs with an Opto-electric probe. The antibody coated sample strips are in embodiments configured to be used either directly for loading the nasal swab sample or as in other embodiments configured to be attached directly to the probe to be inserted inside the nose. In embodiments, the sample strips are coated with an electrode and be configured to conduct current measurements directly, in which case they serve as the probe themselves. This embodiment of probe is configured to be inserted inside the nose, allowing it to touch the nasal wall. In embodiments, the probe is configured to apply current over time continuously through a chip integrated within it, thereby applying an electric field over a sample. Also, an integrated light source and detector is in embodiments incorporated at the other end to conduct light intensity measurements non-invasively.

The concept of strips can be further used to detect different specimens taken from blood, breath, urine, nasal swabs, stool, etc. For example, the test subject can breathe, exhale, or sniff into a device with a probe coated with antibodies, in accordance with embodiments. If binding or interaction with antibodies on the sample strip occurs, embodiments with the integrated device as described above is configured to be able to pick up the interaction, confirming that the patient is infected with the virus to which the antibodies are directed against.

Method and system embodiments are configured such that: a said sample is placed and distributed in one or more microfluidic channels; measurement of said light scattering parameters and/or said electrical parameters is conducted for the sample content in each of said microfluidic channels; and virus concentration and/or virus load is determined based on said measured parameters.

In further variants of such method and system embodiments said sample is diluted such that there is stepwise increasing dilution of antibody content in said one or more microfluidic channels and said measurement of parameters is conducted for said dilution steps.

In method and system embodiments said sample is placed and distributed in a plurality of parallel microfluidic channels; the antibody content is serially diluted in said plurality of parallel channels, simultaneously measuring said parameters in said plurality of channels; and said virus concentration and/or virus load is determined based on said measured parameters.

Method and system embodiments are configured such that the virus concentration and/or virus load is based on a mathematical relationship between said parameters and virus concentration and/or virus load, said mathematical relationship for example being calibrated against known virus concentration or virus load.

Other aspects and embodiments of the invention will be apparent as will be shown in the detailed description of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate non-limiting example embodiments of the invention.

FIG. 2 shows an illustration of the concept of optical detection in accordance with embodiments in an experimental design setup, wherein: FIG. 2(*a*) shows an embodiment of an optical measurement setup consisting of a smart phone as a light source and a mini-spectrometer utilized to collect light waves passing through the sample kept in a holder. FIG. 2(*b*) shows a graph of the smart phone power spectra versus wavelength. FIG. 2(*c*) shows an illustration of the spectrometer detection principle.

FIG. 3 shows graphs of an example of optical responses for spike proteins S1 and S2 along with their corresponding blanks, wherein:

FIG. 3(*a*) shows measured responses for spikes proteins S1 and S2 at the highest concentration individually (S1B and S2B, respectively), along with their corresponding blanks.

FIG. 3(*b*) shows time domain measurements of a microcentrifuge tube.

FIG. 3(*c*) shows measured optical responses for the mixed proteins versus time.

FIG. 3(*d*) shows relative change in light intensity per light path versus loaded mass.

FIG. 4 shows an illustration of light intensity and its path length, wherein:

FIG. 4(*a*) shows a blank representation, and

FIG. 4(*b*) shows the light path length of a sample. L and A are the length and cross-sectional area of container, l is the light path length. $I_0$ is the incident light intensity, $I_b$ is the intensity of light passing through the blank and I instantaneous is the light intensity passing through the sample.

FIG. 4(*c*) shows loaded mass versus relative change in light intensity per light-path length. The measured points have been fitted with exponential function expressed by equation (1) below with the following parameters: $m_i$=1.003μ±2.68n, $m_f$=2.163μ±34.7n and α-factor is 1.28435±0.030. The other fitting model accuracy parameters are: Reduced Chi-Sqr, R-Square (COD), Adj. R-Square are 28.8 atto, 1 and 1, respectively, which indicates the best possible fit.

FIG. 5 shows graphs of optical detection of binding interactions, in this example between ACE2 and other proteins, wherein:

FIG. 5(*a*) shows measured light intensities over time for individual assessment of ACE2, S1A(S1X), S1B(S1Y), and BSA.

FIG. 5(*b*) shows the measured mixed light intensities versus time for ACE2 mixed with either S1A(S1X), or S1B(S1Y), or BSA.

FIG. 5(*c*) shows the measured ACE2-S1A interaction profile for an extended time period.

FIG. 5(*d*) shows extracted slopes for the individual and mixed protein suspensions.

FIG. 6 shows graphs of optical detection of the binding affinities between proteins and antibodies, wherein:

FIG. 6 (*a*) shows the receptor binding domain (RBD) of the spike protein with its antibody (AB).

FIG. 6(*b*) shows the nucleocapsid protein (NCP) and its antibody.

FIG. 6(*c*) shows NCP binding with the antibody after mixing inside.

FIG. 6(*d*) shows NCP binding with the antibody after mixing outside.

FIG. 7 shows graphs of opto-electrical measurements of nucleocapsid protein (indicated NCP or NC protein) with direct current DC biasing, wherein:

FIG. 7(*a*) shows measured NC protein optical response versus time at different DC bias voltages.

FIG. 7(*b*) shows binding measurements between NC protein and its corresponding antibody after subjected the solution to an electric field.

FIG. 8 shows graphs of illustrating examples of protein-protein interaction measurements on paper based nitrocellulose membrane (NM), wherein:

FIG. 8(*a*) shows optical responses on nitrocellulose membrane (NM) alone, nitrocellulose membrane and spike protein (NM+P), and nitrocellulose membrane and antibody to spike protein (NM+AB) alone.

FIG. 8(*b*) shows optical responses to spike protein-antibody binding on the nitrocellulose membrane.

DETAILED DESCRIPTION

Figure 1:
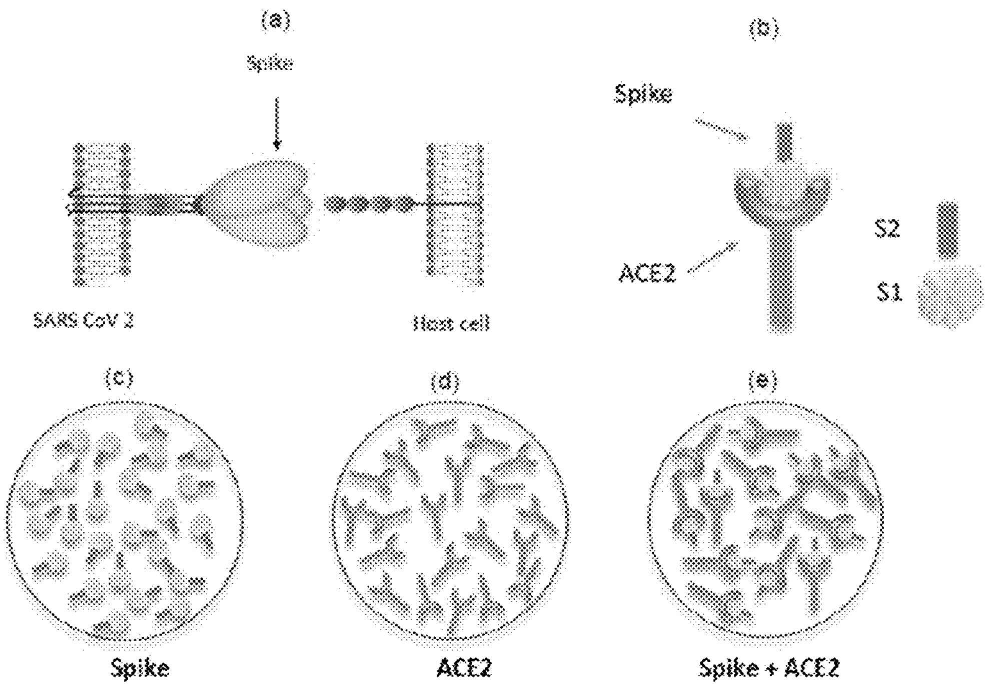
FIG. 1 shows an exemplifying illustration and modelling of binding mechanisms, wherein it is shown in: (a) SARS-CoV-2 binding with host cell illustration. (b) Binding of ACE2 and Spike protein along with illustration of the spike protein subunits, S1 and S2. (c) Schematically showing the distribution of the spike protein in suspension. (d) As an example, schematically showing the distribution of ACE2 in suspension. (e) As an example, schematically showing the distribution of ACE2 and S protein after binding.

Throughout the following description, specific details are set forth in order to provide a more thorough understanding to persons skilled in the art. However, well known elements may not have been shown or described in detail to avoid unnecessarily obscuring the disclosure of embodiments. The following description of examples of the technology is not intended to be exhaustive or to limit the system to the precise forms of any example embodiment. Accordingly, the description and drawings are to be regarded in an illustrative, rather than a restrictive, sense.

Optical, label-free biosensors have been utilized frequently in biomolecular detection due to their continuous monitoring and high sensitivity to local variation, including the refractive index change. They are capable of detecting interactions between molecules and their surrounding media.

On a general level, embodiments comprise a system and a method to detect and possibly monitor the possible binding or interactions between proteins and proteins, proteins and antibody, viruses and proteins, viruses and antibodies, cells and proteins, cells and antibodies. Also, virus-cell, or cell-cell interactions, or any interactions between any part of protein, antibody, virus, cell with any part of protein, antibody, virus, cell of the same or different kind.

Embodiments comprises a method of opto-electrical detection of the presence of possible bindings or interactions between analytes in a sample, comprising: exposing a sample to light from a light source; detecting light passing through the sample; applying an electrical field over the sample; determining the values of a selection of light scattering parameters for the light passing through the sample in response to the electrical field; and/or determining the values of a selection of electrical parameters, such as electrical scattering parameters, in response to the electrical field; determining the presence of bindings or interactions between analytes in the sample based on the values of the determined light scattering parameters and/or the determined values of the electrical parameters, for example electrical scattering parameters.

Further embodiments comprises a system of opto-electrical detection of the presence of possible bindings or interactions between analytes in a sample, comprising: a light source configured to emit or transfer natural or manmade light and to expose a sample with said light; an electric field device configured to apply a biasing electric field over the sample; a light detector configured to detect light passing through a said light exposed sample; an electric parameter detector configured to detect electric parameters. Such embodiments further comprise a processing device having code portions configured direct the processor to: determine the values of a selection of one or more light scattering parameters of the detected light passing through a said light exposed sample; determine the values of a selection of electrical parameters, for example electrical scattering parameters, in response to the electrical field, and to determine the presence of bindings or interactions between analytes in the sample based on the values of the determined light scattering parameters and the determined values of the electrical parameters, for example electrical scattering parameters.

An underlying mechanism for the concept of embodiments is that when two proteins bind or a molecular interaction takes place between them, due to this interaction, a possible form of kinetic energy is produced, perhaps emitted as a cloud. This kinetic energy can cause disturbances, such as altering the Brownian motion of the molecules which can change or alter light distribution on the surface of the sample or inside the sample. The generation of a cloud-like response due to the biochemical interaction should also disturb the light intensity distribution and accordingly the measured light intensities.

Further, the linear electro-optic effect is the change in the index of refraction that is proportional to the magnitude of an externally applied electric field. As mentioned herein. the electro-optic effect may also be non-linear, for example over a wider range. Hence, the measured light intensity varies with DC electric voltage. The DC bias will also change the current and capacitance as they depend on the applied voltage. This relationship/dependency may for example be converted to a chart that could be used for detection enhancement and further identification of the sample under test. For a specific virus type, the corresponding capacitance and light intensity at zero bias could also be used for further detection purposes.

In method embodiments, the presence of bindings or interactions between analytes in the sample is determined is determined based on a determined characteristic of the detected light scattering parameters, and/or electrical scattering parameters for specific values of the electric parameters. In system embodiments, the processing device comprises code portions configured to determine the presence of bindings or interactions in the sample based on determined characteristic of the detected light scattering parameters, and/or electrical scattering parameters, for specific values of the electric parameters.

Method embodiments comprises determining the presence of bindings or interactions between analytes in the sample by comparing the discrepancy between the measured responses at different applied electrical fields. In system embodiments, for this purpose the processing device comprises code portions configured to determine the presence of bindings or interactions between analytes in the sample by comparing the discrepancy between the measured responses at different applied electrical fields. Further method and system embodiments are configured to determine the presence of bindings or interactions between analytes in the sample by comparing the discrepancy between the measured responses at different applied electrical fields; and/or wherein the measured light intensity varies with DC electric voltage and/or values for the capacitance, for example, can be extracted from scattering parameters or impedance measurements or from determined relations between the parameters; and/or to determine information about the viral load and/or identifying the viral stage infection based on the voltage dependency. In embodiments of system, the processing device comprises code portions configured account for these possible features.

The emitted or transferred, manmade or natural, light from the light source may comprise the whole spectrum of wavelengths.

In such method and system embodiments the light detector is one or more of: an image-based system such as a camera, a spectrometer or any light-based detector, sensor or device that is capable to detect light intensity dependent or derivable parameter values. The method and system are in embodiments configured to detect light intensity and to determine light scattering parameters based on one or more of absorbance, reflectance, transmittance or any other type of light scattering, corresponding intensity or other parameter that is extractable or collectable by means of a light detector.

In method and system embodiments a selection of one or more light scattering parameters, for example intensities, are measured and possibly recorded over a time-period and/or mapped to a time domain. In system embodiments the processing device comprises code portions configured to measure and possibly record a selection of one or more light scattering parameters over a time-period and/or to map said parameters to a time domain.

In method and system embodiments the sample is loaded into a transparent holder or container allowing light to pass through the material without appreciable scattering of light and being configured for holding a sample, for example on or more of a plate, box, tube or any type of transparent paper or other transparent material. For this purpose, system embodiments, may further comprise a transparent holder or container allowing light to pass through the material without appreciable scattering of light and being configured for holding a sample, for example on or more of a plate, box, tube or any type of transparent paper or other transparent material.

A sample may, as in method embodiments, be tested in place in close connection with or in the proximity of the taking of the sample or be stored and/or transported for testing spatially and/or temporally remote from the taking of the sample. For this purpose, in system embodiments, the transparent holder or container is configured to store and/or transport a sample.

In method and system embodiments, the light source, a sample and the light detector are aligned such that measurement of light passing through the sample is enabled, for example by alignment in a straight line or other possible such alignment.

The electric field device comprises, in method and system embodiments, two electrodes configured or configurable at respective sides of a sample and being coupled or couplable to an electric energy source.

In method and system embodiments, the sample is added to a holder or container aligned with the light source and the light detector such that measurement of light passing through the sample is enabled; and measured responses in the form of the determined values of said selection of optical or electrical parameters, for example electrical scattering parameters, in response to the electrical field are collected to determine the presence of bindings or interactions between analytes in the sample. In system embodiments, the processing device comprises code portions configured to collect measured responses in the form of the determined values of said selection of optical or electrical parameters, for example electrical scattering parameters, in response to the electrical field for the sample that is added to a holder or container aligned with the light source and the light detector such that measurement of light passing through the sample is enabled.

Such method embodiments comprises steps, and in such system embodiments the processing device comprises code portions, configured to collect measured responses comprising one or more of: collecting directly measured light intensity; and/or collecting directly measured light intensity and establishing direct relationship with time; and/or processing direct measured data to extract parameters or a set of parameters and correlating said parameters with time to establish relationship with the presence of bindings or interactions between analytes in the sample.

Method and system embodiments further comprises determining the type of binding and/or interaction between analytes in the sample based on a relationship between the values of determined light scattering parameters and/or of determined electrical scattering parameters, and time, for example by direct judgement or by further processing. For this purpose, in system embodiments the processing device comprises code portions configured to determine the type of binding and/or interaction between analytes in the sample based on a relationship between the values of the determined light scattering parameters and time, and/or of the electrical scattering parameters and time.

In method and system embodiments, a mathematical relation for the determined parameters represents the process of bindings or interactions between analytes in the sample. For this purpose, in system embodiments, the processing device comprises code portions configured to apply a mathematical relation for the determined parameters to represent the process of bindings or interactions between analytes in the sample.

In examples of such method and system embodiments, with a mathematical relation between determined light scattering parameters, and/or electrical scattering parameters, and time for measured responses at selected applied electrical fields, binding and/or interaction between analytes is determined to be present if the relations shows nonlinearity and not to be present if the relation shows constant behaviour. In system embodiments, for this purpose, the processing device comprises code portions configured to, for a mathematical relation between determined light scattering parameters, and/or electrical scattering parameters, and time for measured responses at selected applied electrical fields, determine that binding and/or interaction between analytes is present if the relations shows non nonlinearity and not present if the relation shows constant behaviour. In case of linear relationship that can be represented with a slope, the two kind of elements or more than two elements under investigation, their individual intensities should be measured and considered accordingly, in method and corresponding system embodiments. Further, in such embodiments the non-linearity may be expressed in terms of extracted single or multi-parameters, the non-linearity may be observed manually or automatically and the variation of response profiles of the one or more parameters may be detected over time. In corresponding system embodiments, the processing device comprises code portions configured to express the non-linearity in terms of extracted single or multi-parameters, to enable the non-linearity to be observed manually or automatically and to detect the variation of response profiles of the one or more parameters over time. Further method embodiments and corresponding system embodiments comprises are configured to determining a mathematical relation for the light scattering parameters, and/or electrical scattering parameters, and values of the electric parameters to represent the presence and/or the process of one or more of said bindings or interactions between analytes in the sample based on the value of light scattering parameters for the detected light passing through the sample.

Method and system embodiments further comprise the use of and configuration with a chronoamperometry or a chronopotentiometry measurement method used to detect and/or monitor the presence and/or the process of one or more of said bindings or interactions.

In method and system embodiments the measured value, for example either current or voltage over time, can be used to explore the interaction. When an interaction occurs, the measured profile over time will increase or decrease in trend, depending upon the nature of the test samples, resulting in either an exponential growth or a decay behaviour. Furthermore, current voltage or capacitance voltage, impedance, or any other possible electrical-based measurements can also be considered. In method embodiments, the presence and/or the process of one or more of said bindings or interactions is determined, detected and/or monitored based on measurements of an electrical parameter, for example an electrical scattering parameter, for example a parameter based on one or more of the voltage, the current, the capacitance and/or the impedance over time in relation to a said applied electric field. For this purpose, in system embodiments, the processing device comprises code portions configured to determine, detect and/or monitor the presence and/or the process of one or more of said bindings or interactions based on measurements of an electrical parameter, for example one or more of the voltage, the current, the capacitance and/or the impedance over time in relation to a said applied electric field.

In further embodiments of method and system, low and high frequency scattering parameters or propagating waves, or any other possible form of measurements can also be considered. For this purpose, method and system embodiments, further comprise or are configured to measure and process parameter values based on low and high frequency scattering parameters or propagating waves.

In method embodiments, and in corresponding system embodiments comprising configured code portions, a characteristic of the determined light scattering parameters, and/or electrical scattering parameters, for specific values of the electric parameters is determined to represent the response of the determined light scattering parameters and/or electrical scattering parameters, due to the possible binding or interaction between one or more analytes in a sample, such as between proteins and proteins, proteins and antibody, viruses and proteins, viruses and antibodies, cells and proteins, cells and antibodies as well as virus-cell, or cell-cell interactions, or any interactions between any part of protein, antibody, virus, cell with any part of protein, antibody, virus, cell of the same or different kind.

Method and system embodiments are configured and/or used to monitor a vaccine or drug development process.

Method and system embodiments described herein may be configured for virus detection. A method embodiment is for this purpose used for virus detection and comprises collecting and processing electrical and optical responses individually or simultaneously to extract a set of parameters for detection, quantification and identification of virus. In a system embodiment for this purpose, the processing device comprises code portions configured to collecting and processing electrical and optical responses individually or simultaneously to extract a set of parameters for detection, quantification and identification of virus. In variants, such method and system embodiments comprise, or are configured to enable that, a virus cell is contacted by a selected antibody in a sample. Variants of such method and system embodiments are further adapted and used for detection of one or more of virus from the group SARS-CoV-2, SARS, MERS, influenza, respiratory syncytial virus (RSV), adenoviruses, or any other respiratory virus.

Further embodiments of the method and the system adapted for virus detection, further comprises or are configured to applying an electrical pulse over or through a sample containing analytes from a test subject and selected antibodies, thereby enabling electro-insertion of said antibodies into any virus cell present in the sample.

In method and system embodiments adapted for virus detection, a virus cell in a sample is suspended in an aqueous transport medium of a nasopharyngeal swab along with anti-N antibodies (anti-N).

In further method and system embodiment adapted for virus detection, the method comprises steps, and the system the processing device comprises code portions, configured to determine a characteristic of the light scattering parameters, and/or electrical scattering parameters, for specific values of the electric parameters and to measure the viral nucleocapsid protein and anti-N antibody interactions in a sample to differentiate between SARS-CoV-2 negative and positive nasal swab samples.

Embodiments of the method and the system adapted for virus detection, further comprises a sample strip configured for collecting a sample of analytes from a test object, the sample strip comprising a portion coated with antibodies. In variants, the sample strip is coated with an antibody configured to bind or interact with of one or more of virus from the group SARS-CoV-2, SARS, MERS, influenza, respiratory syncytial virus (RSV), adenoviruses, or other respiratory virus.

In further method and system embodiments adapted for virus detection, the sample strip comprises an electrode coated thereon and configured to conduct current measurements directly.

Other method and system embodiments for opto-electric virus detection, further comprises a device for nasal sampling configured such that a sampling strip is attachable at a section of the nasal sampling device that is configured to be insertable in the nose of a human test object, the nasal sampling device comprising two electrodes configured to apply an electric field over a sample of analytes collected on a said sampling strip. In such system embodiments the nasal sampling device may further comprise an integrated light source and detector configured to expose the sample to light and to detect light passing through the sample.

Such integrated method and system embodiments are, in variants, configured such that when the presence of a binding or interaction between a virus and an antibody is detected in a sample from a patient, an indication signal is presented confirming that patient is infected with the tested virus. The indication signal for infection may for example be in the form of light, sound, text or image presented via a corresponding presentation device.

In embodiments of method and system, a sample is taken from bodily tissue or fluid, for example blood, breath, urine, nasal swabs, stool, in the system embodiments with a strip configured for this purpose.

These method and system embodiments are further described and explained by illustrating examples below.

FIG. 1 shows an exemplifying illustration and modelling of binding mechanisms of virus to surrounding media. FIG. 1(*a*) schematically illustrates SARS-CoV-2 binding with a host cell. FIG. 1(*b*) In this example, binding of ACE2 (angiotensin converting enzyme 2) and Spike protein along with illustration of the spike protein subunits, S1 and S2. FIG. 1(*c*) schematically shows the distribution of the, in this example, spike protein in suspension. FIG. 1(*d*) schematically shows the distribution of ACE2 in suspension. FIG. 1(*e*) In this example, schematically shows the distribution of ACE2 and S protein after binding in suspension.

There are several antigens and elements that in SARS-CoV2 virus that are active in binding and/or interaction, ACE2 is one example, nucleocapsid is another example and the technology of the present disclosure is applicable to other antigens and elements as well. The technology of embodiments disclosed herein can, as described herein, be applied on any virus, antigens, antibodies or elements.

For the sake of example, embodiments herein are explained with application of the technology on ACE2 and nucleocapsid. In terms of detection, one of the most prominent features of the SARS-CoV-2 virus, like other coronaviruses, is the spike protein (S) that protrudes out of the virus particle essentially like "spikes"; hence the name. The spike protein forms a trimer that is used by the virus to enter susceptible cells using the angiotensin-converting enzyme 2 (ACE2) protein as the cellular receptor, the same protein used by the SARS-CoV-1 virus that caused the first SARS epidemic in 2003 (FIG. 1(*a*)). The spike protein is cleaved by host cell membrane proteases into two subunits: the surface subunit S1, and the transmembrane subunit S2 (FIG. 1(*b*). It is the surface S1 subunit that is used by the virus to interact with ACE2 protein using its receptor binding domain (RBD). This allows the virus to attach to the susceptible cells, while the S2 protein is used for the actual fusion of the virus with the cell membrane, allowing the virus to be endocytosed into the cytoplasm and release its genomic RNA cargo, wrapped up in the nucleocapsid protein (NCP), into the cytoplasm. It is this RNA that is immediately used to translate viral proteins and use them for successful virus replication in the susceptible cells. The spike protein is also the most immunogenic domain of the virus towards which most of the neutralizing antibody responses against the virus are generated in infected individuals, making it an ideal candidate for vaccine as well as a target of drug development. In the context of COVID-19, it has been observed that the SARS-CoV-2 spike glycoprotein binds ACE2 with much higher affinity than SARS-CoV-1 spike protein, which may explain the higher transmissibility of SARS-CoV-2 in the human population.

Embodiments described herein, comprises a light-based method to detect SARS-CoV-2 and potentially disrupt its binding ability with its receptor, rendering the virus non-infectious by combining optical detection with electric current. The measured intensity of light is used to determine information about different cellular parameters in a sample under study with method embodiments. Light scattering and electrical scattering are correlated with cell/virus size and reflect the complexity of their exterior or interior structures. When light passes through a cell, the intensity is associated with the DNA/RNA content of the cells. The nuclei size, cell shape and the refractive index variation of cells contribute to light intensity in the cell. It is worth adding that the measured optical spectrum of light passing through a sample consists of many features that in embodiments is used to reveal and determine important information about the sample under test. Usually when the cell/tissue changes from a normal state to infectious, metabolic alterations and genetic modifications occur. This causes dramatic changes in their physiological, biochemical and morphological characteristics. Indeed, the metabolic differences between infected and normal cells leads to several variations in cellular parameters, such as their size. In this text, embodiments with an optical label-free detection method incorporating a smartphone light source and a portable mini spectrometer for SARS-CoV-2 detection are described. The detection of parameters reflecting light interactions with control and viral protein solutions in accordance with embodiments enables a quick decision regarding whether a sample under test is positive or negative, thus enabling SARS-CoV-2 detection in a rapid and label-free manner.

Figure 2A:
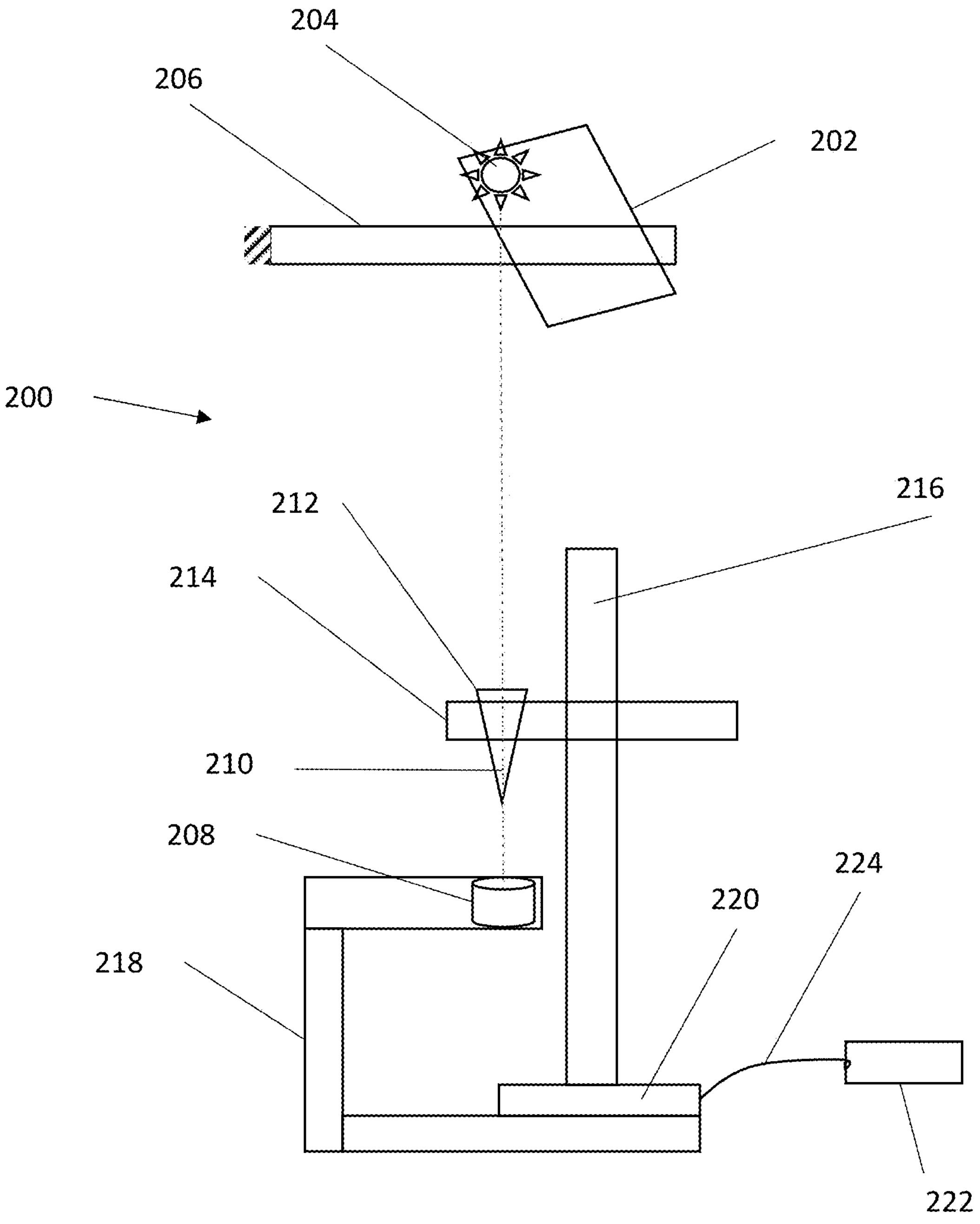
Figure 2B:
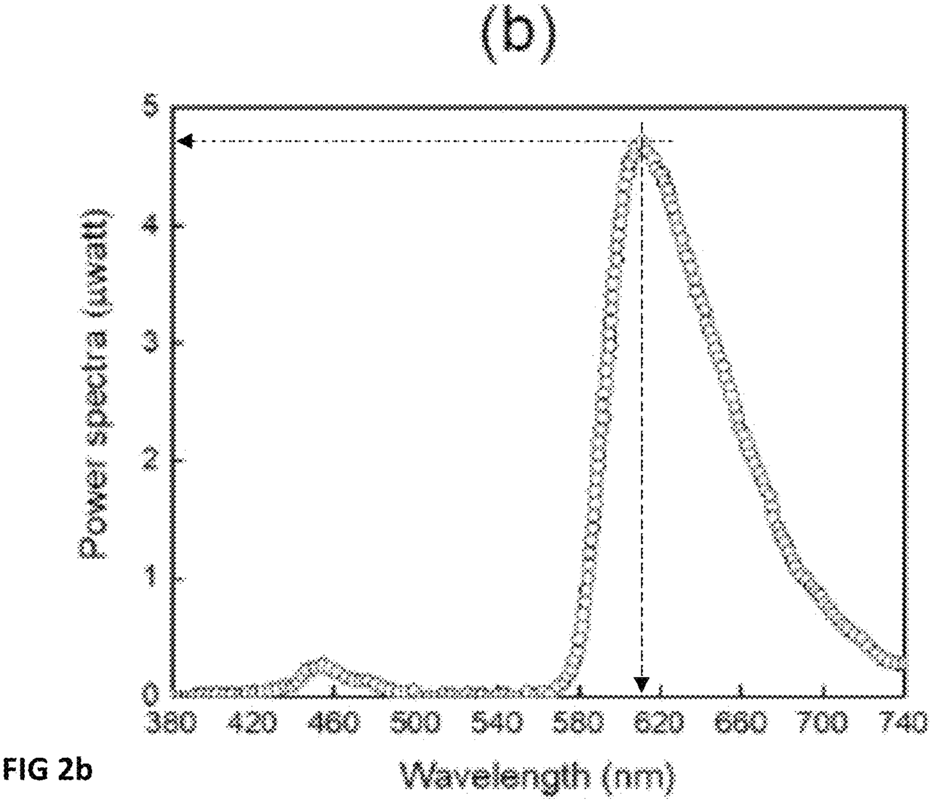
Figure 2C:
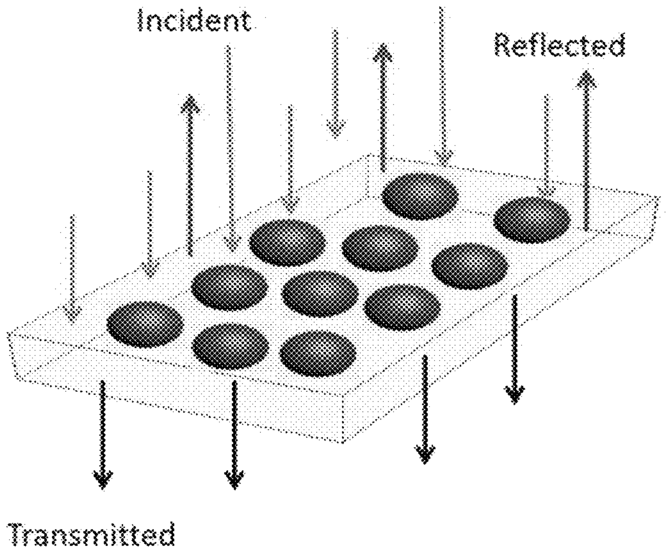
Figure 3A:
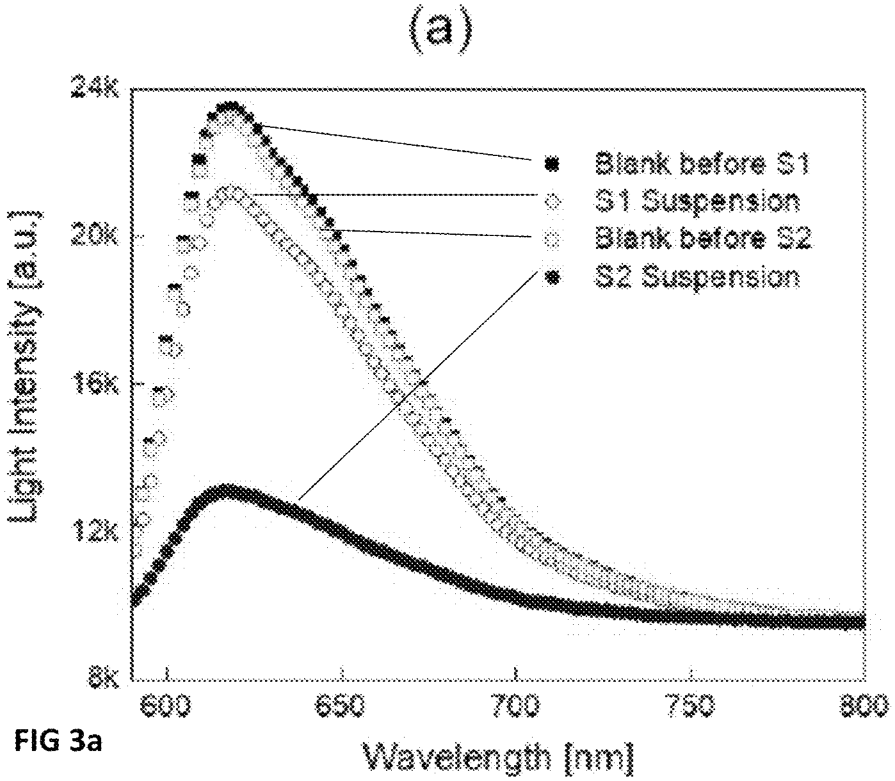
Figure 3B:
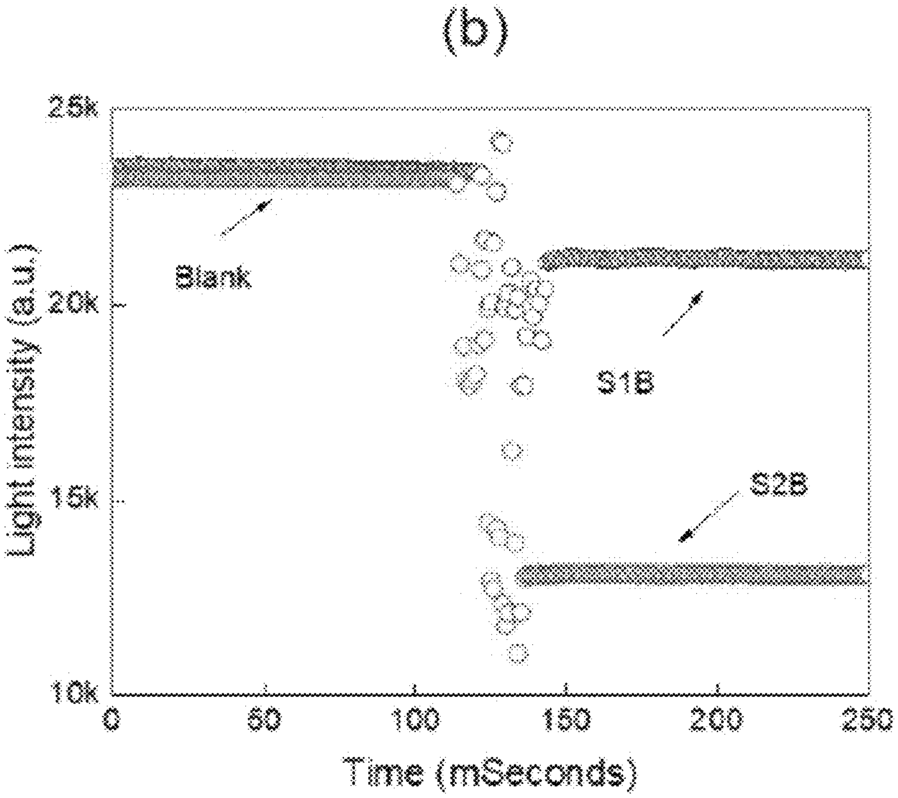
Figure 3C:
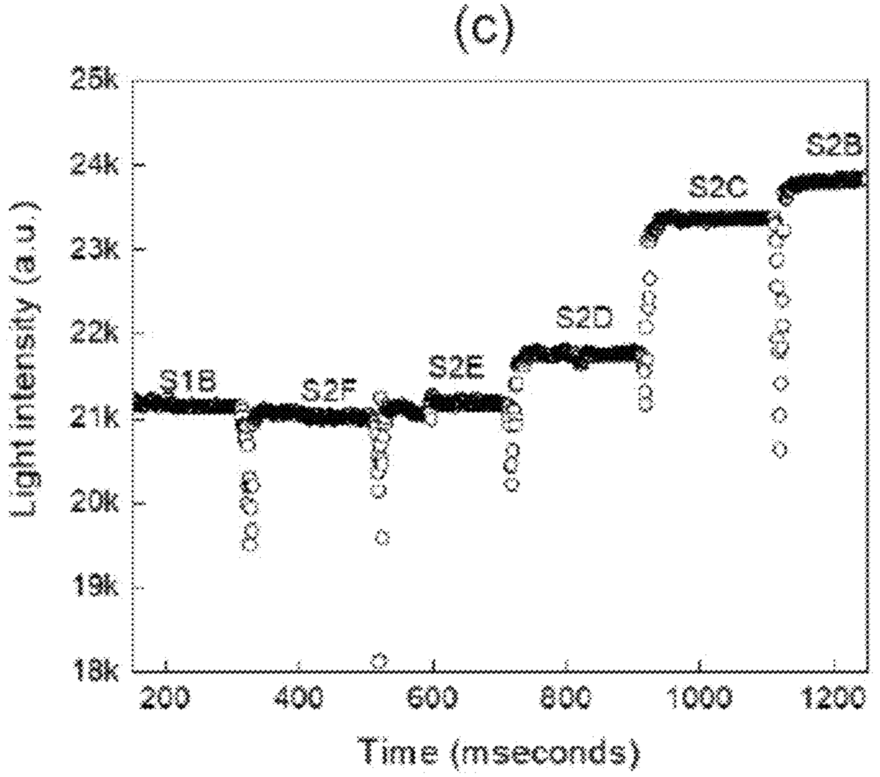
Figure 3D:
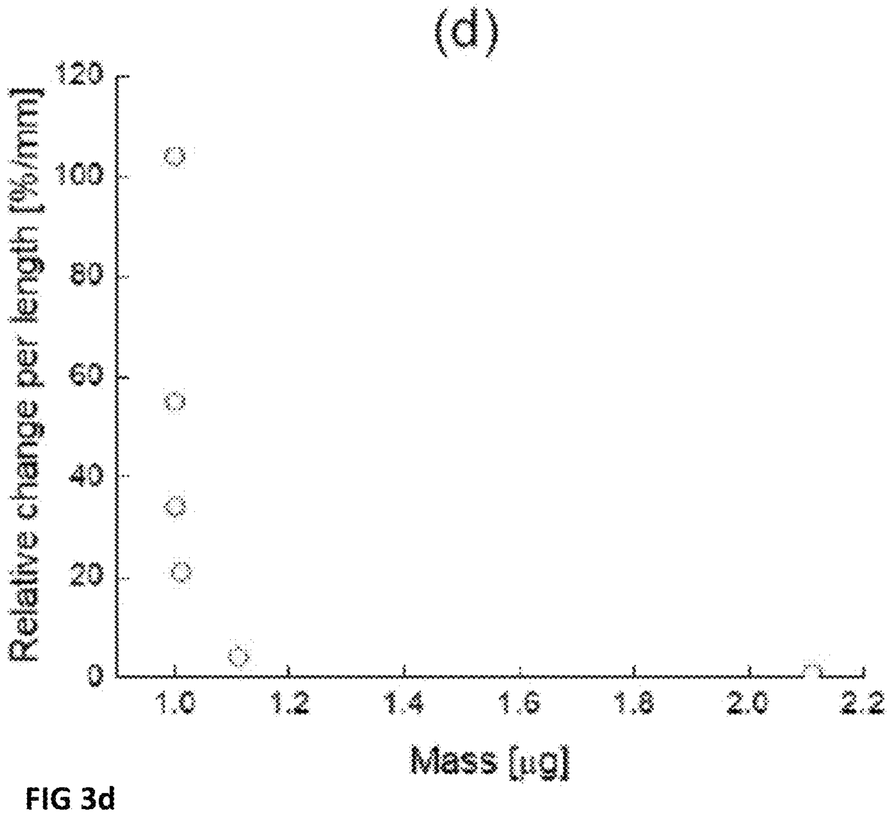

FIG. 2 illustrates a concept of optical detection in accordance with embodiments in an experimental design setup. FIG. 2(*b*) shows a graph of the smart phone power spectra versus wavelength and FIG. 2(*c*) shows an illustration of the spectrometer detection principle.

An experimental setup utilized to illustrate an exemplary embodiment presented in FIG. 2(*a*), incorporating a mini spectrometer and a smart mobile phone that was employed as a light source with the power spectrum depicted in FIG. 2(*b*). FIG. 2 (*a*) thus shows an embodiment of an optical measurement setup 200 comprising a smart phone 202 with a built in LED-light as a light source 204. The light source 204 is, with the smart phone mounted on fixture 206, aligned with a spectrometer in the form of a mini-spectrometer 208 utilized to collect light waves passing through a sample 210 to be analysed. The sample 210 is kept in a container 212 in the form of a cuvette placed in a holder 214 that is mounted on a stand 216. The mini-spectrometer 208 is mounted in a spectrometer stand 218 with its electronics 220 coupled to a PC 222 or other control or processing device via control and/or data cable 224.

The graph in FIG. 2(*b*) shows the smart phone power spectra versus wavelength in an example of the experimental setup. In one example the measured optical power of the light beam exhibited a maximum power of approximate 35 μW at a wavelength of 623 nm, and in another example a maximum power of 47 μW at a wavelength of 615 nm as indicated in the graph of FIG. 2(*c*). In examples a mini-spectrometer C11708MA (Hamamatsu/Japan) was used to measure the light intensity as the light passes through test substances with spectral response ranging from 640 to 1010 nm. In those examples the wavelength reproducibility varied between −0.5 to 0.5 nm and a maximum of 20 nm full width at half maximum FWHM spectra, under constant light conditions. The sample under test was placed between the, in this example mobile, light source and the minispectrometer, as described and as shown in FIG. 2(*a*). The measurements were conducted with the room lights on. The distances between the light source, the spectrometer, and the sample holder were adjusted to eliminate any possible interference and to stabilize the spectrometer performance.

FIG. 2(*c*) illustrates the incident, reflected, and transmitted light intensities. The spectrometer was aligned with the light source and a sample cuvette accommodating the sample to achieve a straight path of light. The light intensities were linked through the Kirchhoff's Law of Radiation, which correlates the optical absorbance (A), transmittance (T), and reflection (R) along with the incident wave (I). In this text, the percentage of the relative change in light intensity ($\Delta I_r$) is introduced and defined to be the difference between the two measured peaks divided by their maximum peak times 100%.

An experimental setup in accordance with this embodiment may be used to characterize the two spike proteins subunits, S1 and S2 that are encoded by all coronaviruses and allow virus entry into susceptible cells, as illustrated in FIG. 1(*b*). FIG. 3(*a*) shows an example of the optical responses for both spike proteins S1 and S2 along with their corresponding two blank samples. The measured optical intensity changed from 600 to 750 nm, within the light source spectrum measured earlier as illustrated in FIG. 2(*b*). The response of the blank samples was performed first, followed by the samples with the two protein suspensions, the responses to which were recorded individually.

The graphs in FIG. 3 show examples of optical measurements of samples with the spike protein subunits S1 and S2 in a microcentrifuge tube, wherein:

FIG. 3(*a*) shows measured light intensity over wavelength responses for spike proteins S1 and S2 at the highest concentration individually (S1B and S2B, respectively), along with their corresponding blanks.

FIG. 3(*b*) shows time domain measurements of the corresponding samples, the blank here an empty microcentrifuge tube shown to the upper left and the S1B sample with water to the upper right in grey circles, versus the blank again an empty microcentrifuge tube before S2B to the upper left and the S2B sample with water to the lower right in red circles, at a wavelength of 623 nm.

FIG. 3(*c*) shows measured optical responses for the mixed proteins versus time. Samples S1 and S2 were at 5000 copies per ml, S2C, S2D, S2E and S2F are the serial dilutions of S2B at 10-, 100-, 1,000- and 10,000-fold, respectively.

FIG. 3(*d*) shows relative change in light intensity per light path versus loaded mass. All optical responses were measured at 623 nm. Light intensity was measured as arbitrary units (a.u).

FIG. 3(*a*) reveals that S2 exhibited a higher “back scattering” or absorbance than S1. The response of the two blank samples was quite comparable, showing the reproducibility of the results. Since the maximum difference between the blank and the two protein samples was observed at 623 nm, this wavelength was chosen for further experimentation to illustrate embodiments, which is also the wavelength at which the optical power of the smart phone is at its maximum.

Optimization of the Sample Reading Conditions

Embodiments comprise calibrating a system for opto-electric virus detection in order to correct for errors that may occur when samples are loaded into the sample holder, and the angle and position of a container for a sample for example in the form of a microcentrifuge tube changes which may affect the results obtained. To ensure that the results are reproducible, the measurements for the same samples may, as in embodiments, be conducted over different days. In such embodiments the setup may be standardized for example on each day since the position of the mobile phone, spectrometer and/or samples may vary. To overcome this caveat and have more consistence measurements without constant standardization, advantage may be made of the ability of the spectrometer to provide light intensity measurements over time. Hence, after placing the microcentrifuge tube into the holder, the measurement mode may be started and the corresponding “blank” recorded. Then the sample would be added after for example ~1.5 seconds, while keeping the measurement mode on. FIG. 3(*b*) illustrates the corresponding measurement profile for the buffer, in this case water. As would be expected, the blank exhibited the maximum measured light intensity, while the water sample showed lower light intensity than the blank. The shift in response time due to loading of the sample ranged between 1.5 to 2.3 seconds.

Test of the Spike Proteins Using the Experimental Set Up of Embodiments

In an example of conducting a test on the proof-of-principle of these embodiments for experimental design, initially a mixing experiment was conducted at a light wavelength of 623 nm. Towards this end, 250 μL of S1 protein solution was tested at the same maximum concentration at 5,000 copies/mL followed by addition of same amount of S2. FIG. 3(*c*) shows the light intensity (as arbitrary units, a.u.) with time as the protein samples were added to the container in a sequential manner. This was followed by addition of 250 μL of ten-fold serial dilutions of the S2 protein at equal time intervals to the S1+S2 samples. As can be seen from FIG. 3(*c*), with the addition of the S2 protein, the light intensity increased. The biggest increase was observed with the concentrated S2 sample followed by its ten-fold dilution samples S2A, S2B, S2C, etc., until S2F addition as a 1:10,000 dilution had no extra effect on the increase in light intensity, indicated the limit of detection of the assay to be 5000 molecules per mL×250 μl×1/10, 000=125 molecule per mL. These results indicated that ratio between the S1 and S2 protein concentration plays an important role in the light intensity levels measured. The ratio of S1 and S2 in the virus is the same since both come from the cleavage of S protein. However, the S1 subunit is expressed on the cell surface, while the S2 subunit is embedded in the lipid bilayer of the cell membrane; therefor S2 is less available at the cells surface, which should affect light intensity less than S1 despite equal ratios.

Table 1 below lists the extracted parameters at specific time points. The relative change in light intensity per light path length is a constructed parameter that should correlate with the loaded mass (concentration) of the protein in a suspension.

TABLE 1

List of measured and extracted parameters.

| Sample description | Light Intensity [a.u.] | Length of the Light Path [mm] | Mass of Protein Tested [μg] | $\Delta I_r$ per length [%/mm] |
|---|---|---|---|---|
| S1B | 21215 | 0.11111 | 1 | 104 |
| S1B + S2F | 21080 | 0.22222 | 1.0001 | 55 |
| S1B + S2E | 21265 | 0.33333 | 1.0011 | 34 |
| S1B + S2D | 21785 | 0.44444 | 1.0111 | 21 |
| S1B + S2C | 23440 | 0.55556 | 1.1111 | 4 |
| S1B + S2B | 23875 | 0.66667 | 2.1111 | 0.8 |

FIG. 3(*d*) shows the change in relative light intensity versus the total mass of the tested samples. As shown in Table 1, it indicates that as the mass of the protein increased in our experimental system, the intensity of light also increased, irrespective of the nature of the protein.

Figure 4A:
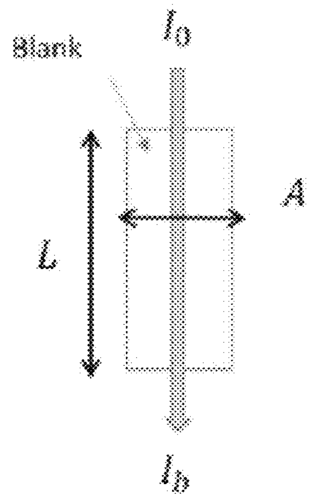
Figure 4B:
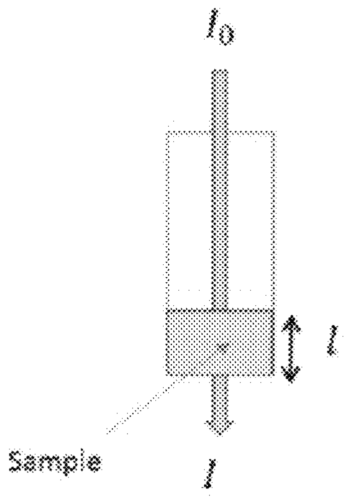
Figure 4C:
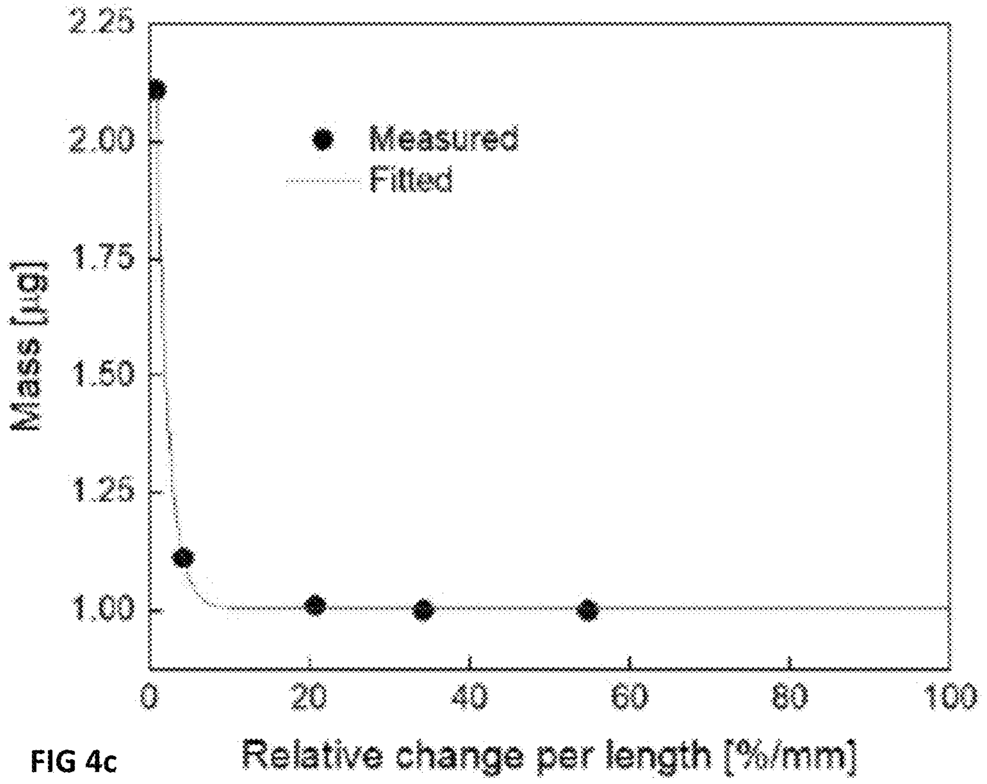
Figure 5A:
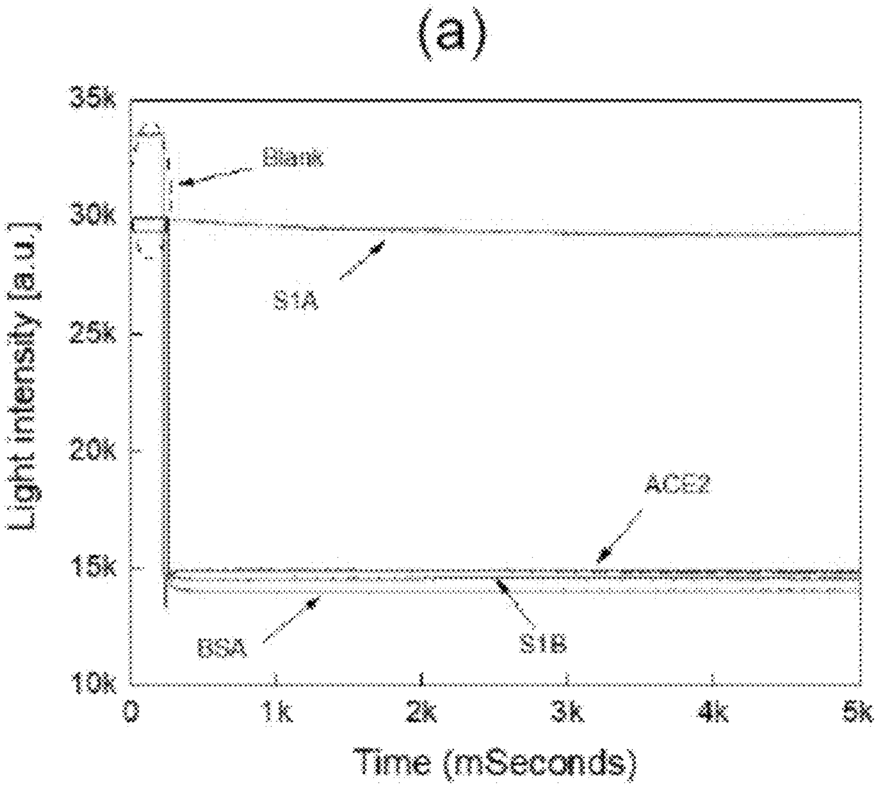
Figure 5B:
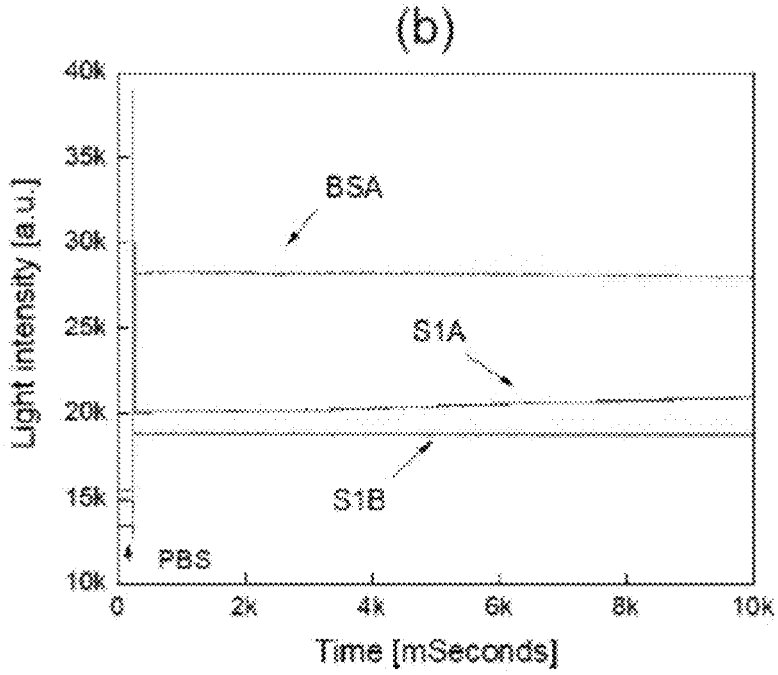
Figure 5C:
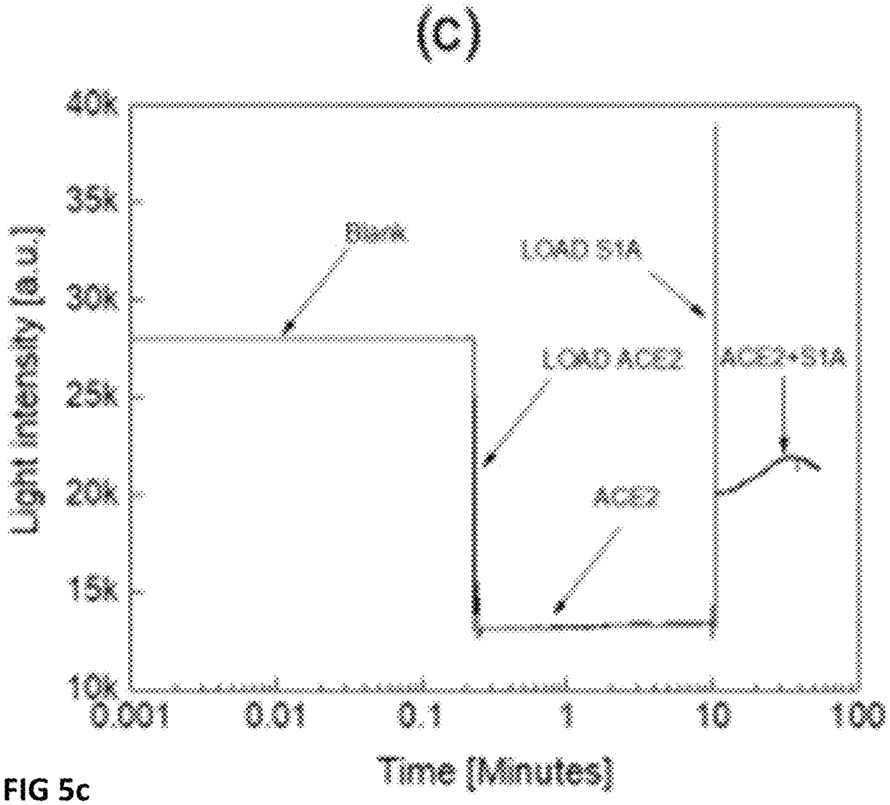
Figure 5D:
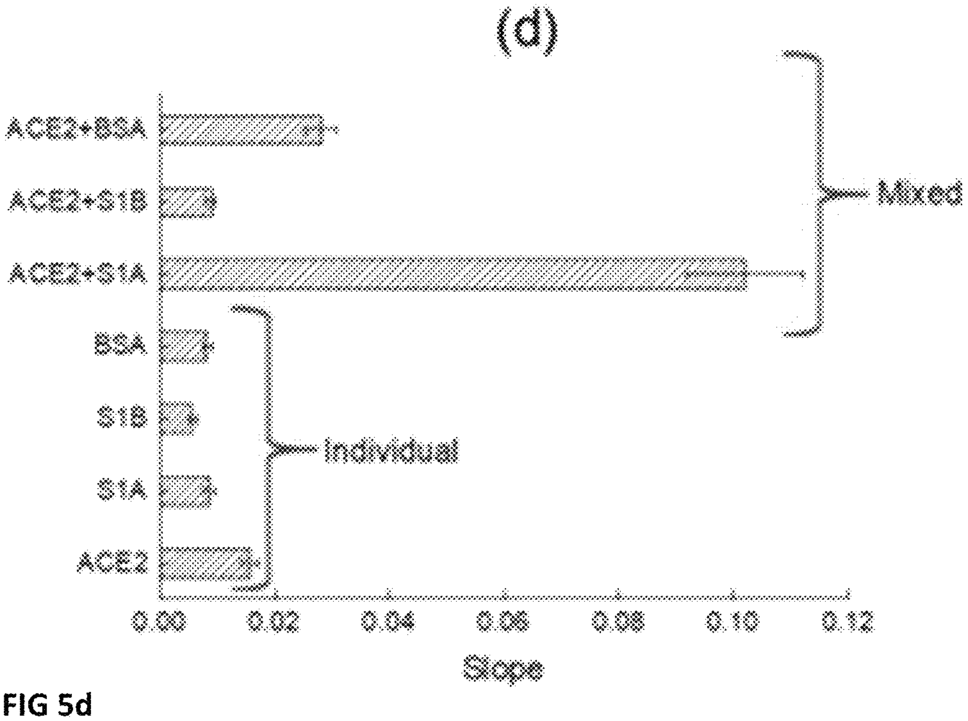
Figure 6A:
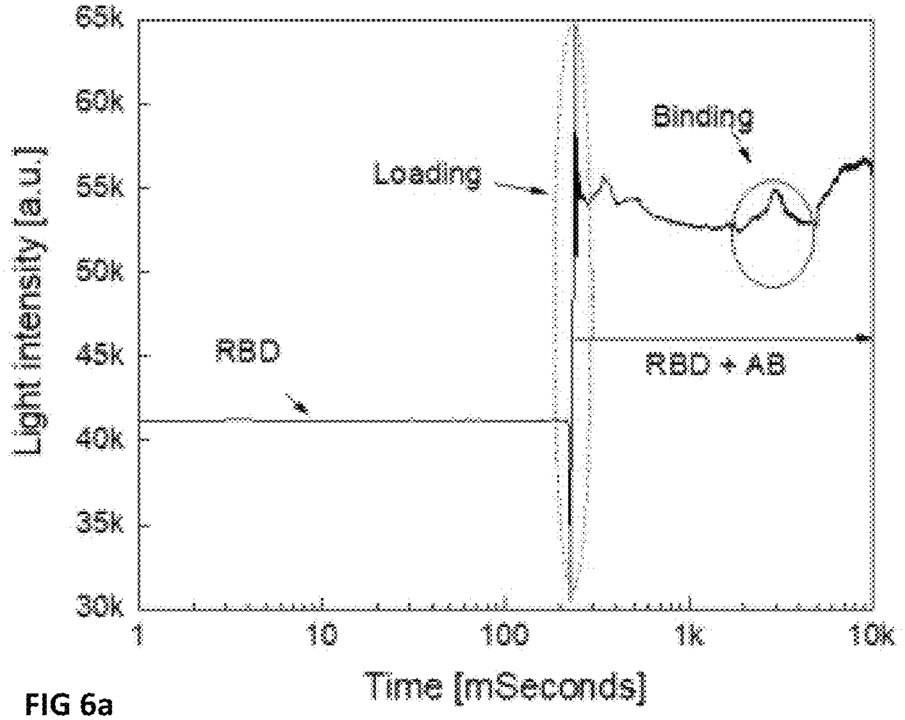
Figure 6B:
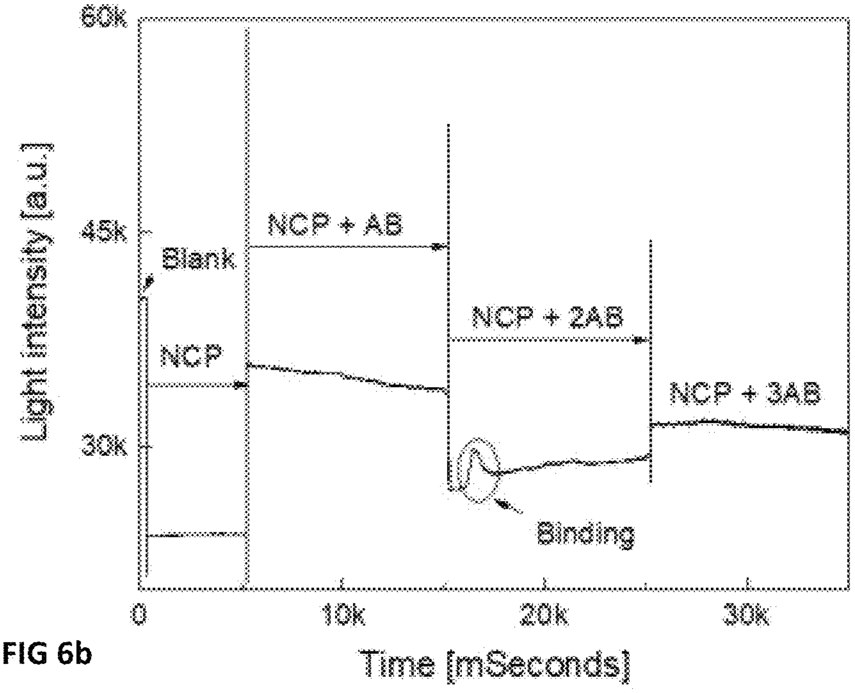
Figure 6C:
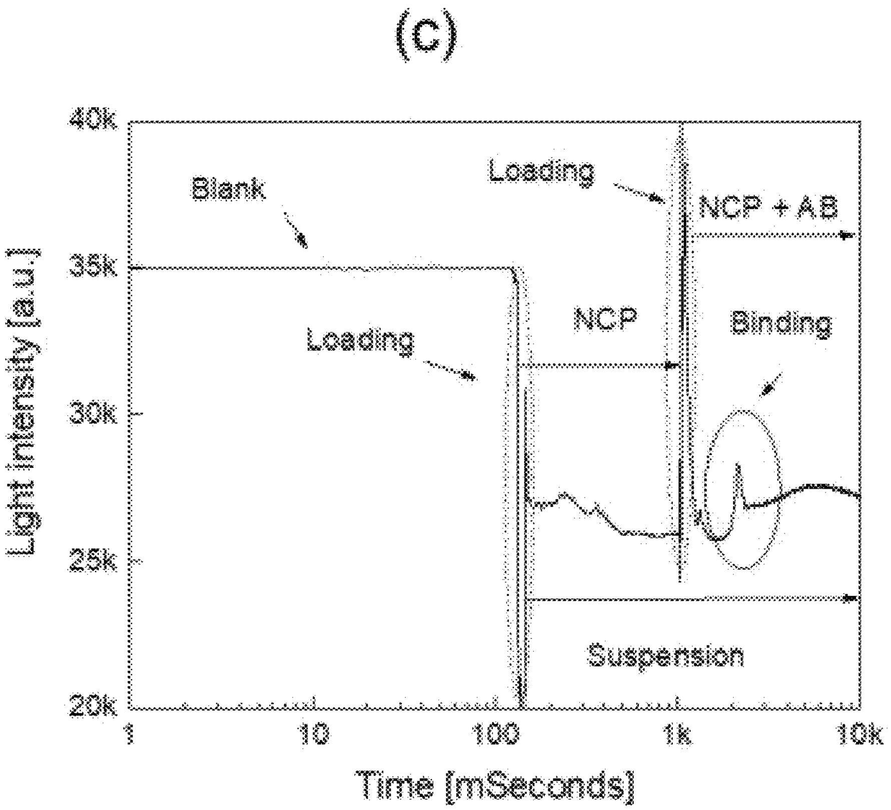
Figure 6D:
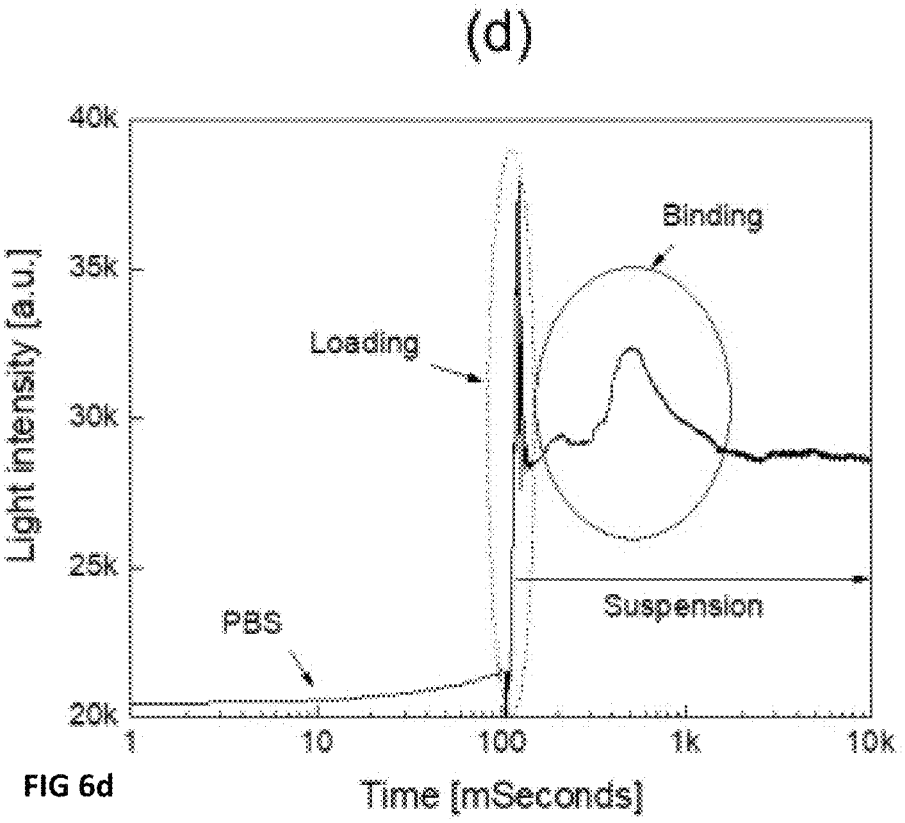

FIGS. 4(*a*) and (*b*) illustrate the definitions of the light intensities and light path length. The light source, for example a smart mobile integrated light source, emits a light intensity ($I_0$) that is the maximum intensity that can be measured in an experimental setup in accordance with the above embodiments. The blank intensity ($I_b$) is the measured intensity that goes through the empty container holding the sample such as the microcentrifuge tube used in the examples above. The instantaneous intensity (I) is the recorded light when it passes through the sample. This amount of light intensity strongly depends upon the buffer in which the sample is solubilized/dissolved in, its composition, the light path length, the kind of the suspended analytes and its size in the buffer. The light path length depends upon the loaded amount of suspension inside the container. The path length varies from zero up to the container length (L). For a sample with a specific volume (V), the corresponding path length is equal to the volume over the cross-sectional area of the container (A). Equation (1) expresses the relationship between the relative change in light intensity per light path length and loaded mass (m), as follows in equation (1):

$$m=m_i+m_f e^{-\alpha(\Delta I/l)} \quad (1)$$

In equation (1): $m_i$, $m_f$ and l are the initial mass of the buffer, the mass of the final suspension composite, and the light path length, respectively. α is the decay factor, unique for each control buffer. Its unit is in mm and could be correlated with the material absorptivity. ΔI is the relative changes in light intensity expressed as follows in equation (2):

$$\Delta I=(1-I/I_b)\times 100\% \quad (2)$$

In equation (2): I and $I_b$ are the instantaneous measured light intensity of the suspension and the corresponding blank, respectively. FIG. 4(*c*) shows the relationship between mass and the relative change per length after fitting the measured points with the exponential function. As can be seen, with more sample volume the path length increases and light intensity decreases, hence relative change decrease dramatically.

In method and system embodiments, relations for example those described herein, above and/or below, are applied to determine concentration of virus or virus load by serial dilution of antibody and simultaneous measurements using one or more microfluidic channels filled with a virus sample in solution. A microfluidic sensing device comprised in embodiments comprises one or more microfluidic channels. In the case with a plurality of microfluidic channels, the channels are in preferred embodiments arranged in parallel.

A light source may as in some embodiments integrated with the microfluidic sensing device, or the microfluidic sensing device may as in other embodiments be configured to receive light from an external light source. Both variant embodiments are configured such that light passes through the sample in each of the one or more microchannels, or groups of microchannels.

Embodiments of such microfluidic sensing devices further comprise an electric field device configured to apply an electric field over individual microchannels or groups of microchannels. Such an electrical field device may be integrated in the microstructure of the microfluidic device or be configured as a device external to the microstructure of the microfluidic device. The electrical field device may comprise electrodes and/or electrode connectors configured for individual channels, groups of channels or the whole microstructure.

Embodiments of such a microfluidic sensing device comprises a light sensor and/or an electrical sensor. Such sensors may be integrated in the said one or more channels or in the microstructure surrounding the channels, and said sensors are configured such that they can measure light and/or electrical parameters, e.g., scattering parameters, for each individual microchannel or groups of microchannels.

Mathematical models based on such said relations are used to extract a measurement value for the concentration of virus or virus load in the sample, thus reflecting the concentration of virus or virus load of test subject or patient from which the sample is taken. Quantification of the measurement value is for example carried out by means of calibration values e.g., represented in curves or tables. Such calibration values can for example be generated by calibrating parameter values determined in accordance with embodiments herein with known values for virus concentration or virus load. In embodiments, a quantification of concentration of virus concentration or virus load is determined from the differences of capacitance voltage profiles, and by processing a difference signal using semiconductor theory to extract single parameters or a collection of multiple parameters to determine said virus concentration or virus load.

Variants of these microfluidic channel embodiments, as with other embodiments herein, are configured to use for the detection of for SARS-CoV-2 diagnosis, whereas other variants are configured, dependent on selection of the antibody used, for detection of any respiratory virus such as influenza, respiratory syncytial virus (RSV), adenoviruses, or other coronaviruses like SARS and MERS.

Method embodiments for these purposes are configured such that: a said sample is placed and distributed in one or more microfluidic channels; measurement of said light scattering parameters and/or said electrical parameters is conducted for the sample content in each of said microfluidic channels; and virus concentration and/or virus load is determined based on said measured parameters.

In further variants of such embodiments said sample is diluted such that there is stepwise increasing dilution of antibody content in said one or more microfluidic channels and said measurement of parameters is conducted for said dilution steps.

In method embodiments said sample is placed and distributed in a plurality of parallel microfluidic channels; the antibody content is serially diluted in said plurality of parallel channels, simultaneously measuring said parameters in said plurality of channels; and said virus concentration and/or virus load is determined based on said measured parameters.

In further variants of the methodd the virus concentration and/or virus load is based on a mathematical relationship between said parameters and virus concentration and/or virus load, said mathematical relationship for example being calibrated against known virus concentration or virus load.

System embodiments for the above purposes, comprise: a microfluidic sensing device with one or more one or more microfluidic channels configured for placing and distributing a said sample in one or more of said microfluidic channels; one or more sensors configured for measurement of said light scattering parameters and/or said electrical parameters for the sample content in each of said microfluidic channels; and code portions, in said processing device, configured to determine virus concentration and/or virus load based on said measured parameters.

Further variants of system embodiments are configured for dilution of said sample such that there is stepwise increasing dilution of antibody content in said one or more microfluidic channels and said measurement of parameters is conducted for said dilution steps.

In further system embodiments: said microfluidic sensing device is configured with a plurality of parallel microfluidic channels for placing and distributing said sample; said microfluidic sensing device is configured for serially diluting the antibody content in said plurality of parallel channels, simultaneously measuring said parameters in said plurality of channels; and said system is configured to determine said virus concentration and/or virus load based on said measured parameters.

In some such system embodiments, said code portions are configured such that the virus concentration and/or virus load is based on a mathematical relationship between said parameters and virus concentration and/or virus load, said mathematical relationship for example being calibrated against known virus concentration or virus load.

These embodiments with microfluidic channels may be applied in conjunction with other embodiments described herein or independently.

Above it is described by means of exemplifying embodiments how to detect proteins in solution using light. Further, as in embodiments described herein, light intensity is used to characterize the binding interactions of the spike protein with the viral receptor ACE2. As an exemplifying demonstration of this mechanism, two different variants of the S1 subunit of the spike protein, S1A(S1X) and S1B(S1Y), were tested. One of these variants could bind ACE2 with a much stronger affinity than the other one. The S1 subunit of the spike protein S1A and S1B were tested along with a non-specific control protein, bovine serum albumin (BSA) that should not bind to ACE2. These proteins were selected to demonstrate the detection of the binding process with ACE2 over time. Examples of measurement results are shown in FIG. 5 with graphs of optical detection of binding interactions between ACE2 and other proteins. FIG. 5(*a*) shows measured light intensities over time for individual assessment of ACE2, S1A, SIB, and BSA. FIG. 5(*b*) shows the measured mixed light intensities versus time for ACE2 mixed with either S1A, or S1B, or BSA. FIG. 5(*c*) shows the measured ACE2-S1A interaction profile for an extended time period. FIG. 5 (*d*) shows extracted slopes for the individual and mixed protein suspensions.

The measurement process in this example started with the blank, and after 200 seconds, 250 μL of ACE2 protein suspension was tested, as depicted in the graph of FIG. 5(*a*). This process was repeated for S1A (S1X), S1B (S1Y), and BSA and their responses to light were measured individually in the same manner as ACE2.

The corresponding individual profiles of ACE2, S1A (S1X), S1B (S1Y) and BSA are depicted in FIG. 5(*a*) which showed a straight constant line over time. The responses of the various protein mixtures were read over a period of 15 minutes and are shown in FIG. 5(*b*). This is interpreted to mean that there was no protein-protein interaction if the line was straight and constant, otherwise protein-protein interaction occurs.

To explore the interaction and binding characteristics, by example between ACE2 and S1A (S1X) in more detail, the measurement time between the two proteins was extended over one hour the results of which are plotted in FIG. 5(*c*). As can be seen, a nice "hump" was observed as an increase in arbitrary units with time that was not observed in the other protein mixtures tested. The corresponding intensity of the interaction ($I_{ia}$) versus time (t) was fitted with a quartic polynomial as follows in equation (3):

$$I_{ia}=a+bt+ct^2+dt^3+et^4 \quad (3)$$

In embodiments the following coefficients in equation (3) have the values: a, b, c, d and e are 20215.00393±6.54838, $-0.15559\pm9.83118\times10^{-4}$, $1.70666\times10^{-5}\pm5.093\times10^{-8}$, $-4.41996\times10^{-10}\pm1.09328\times10^{-12}$ and $3.46019\times10^{-15}\pm8.30214\times10^{-18}$, respectively. These coefficients can be used in embodiments to detect and identify the kind of analyte that binds with the ACE2 receptors. With other antigens and elements, the coefficients would have values characterised by the specific antigens or elements.

FIG. 5(*d*) shows the corresponding slopes that represent the change of the light intensities over time. Next, each protein was mixed with, in this example, the ACE2 antigen separately to detect any possible binding effect. The measurements started with first loading the ACE2 in the blank container, then after 200 ms, each protein was added to the ACE2. The ACE2+BSA and ACE2+S1B (S1Y) responses exhibited almost constant lines with corresponding responses shown in FIG. 5(*d*), suggesting highly reduced or lack of any interaction as observed when the proteins were tested individually. However, the ACE2+S1A (S1X) profile showed a linear straight line with the maximum-recorded slope. The corresponding light intensity line increased over time, suggesting an interaction between the S1A (SIX) protein and the ACE2 receptor. It is noticeable that the slopes of the mixed proteins with ACE2 that did not exhibit much interaction, i.e., S1B (S1Y) and BSA, their slopes after mixing were less than the sum of their individual slopes. On the other hand, the ACE2+S1A (S1X) slope was higher than the sum of the individual ACE2 plus S1A (S1X) slopes, revealing a synergistic effect on light intensity. Based on these observations, our results suggest that the S1A (S1X) protein exhibits stronger interactions with ACE2, while BSA and S1B (S1Y) had weaker interactions with ACE2. These observations are confirmed by the fact that whereas S1A (S1X) has a higher affinity for ACE2 (for example 2 μg/mL S1A can bind 1.5-15 ng/mL ACE2), S1B (S1Y) reportedly has a much lower affinity (for example 2 μg/mL S1B binds 0.5-8.7 ng/mL ACE2), as tested in enzyme-linked immunosorbent assays (ELISA) by the company that synthesized these proteins (ProSci, USA).

In further embodiments, the described optical system is used to detect protein-protein interactions. Using proteins that are well known to interact with each other in such measurements confirm the results described above. In an example, this can be done by testing the molecular interactions between an antigen and an antibody which is similar to the interaction between the spike protein and its receptor. In such an example, two proteins were tested along with their specific antibodies: the first protein was the receptor binding domain RBD of SARS-CoV-2 spike protein and its antibody and the other was the nucleocapsid protein NCP of SARS-CoV-2 and its antibody. Similar to the procedure described above, the two proteins were tested individually in an optical assay as described above followed by addition of their corresponding antibodies that were mixed and their interactions. FIG. 6 shows graphs of optical detection of the binding affinities between proteins and antibodies in this example. FIG. 6(*a*) shows the binding between the receptor binding domain RBD, in this example, of SARS-CoV-2 spike protein and its antibody AB. Upon the addition of the antibody, marked Loading in FIG. 6(*a*) an interaction peak was recorded as indicated with a circle FIG. 6(*a*).

FIG. 6(*b*) shows the binding between, in this example, the nucleocapsid protein NCP of SARS-CoV-2 and its antibody AB. As indicated in the graph, the measurement started with a blank, then with added NCP and after that with added antibody NCP+AB three times, indicated NCP+AB, NCP+2AB and NCP+3AB, respectively. The antibody was added a second time to NCP since no binding interaction was observed the first time. After the second addition of antibodies 2AB a peak in the light intensity indicating binding activity was observed, as indicated with a circle in FIG. 6(*b*). To further confirm the result, the antibody was added a third time NCP+3AB, and this time once again, the binding interaction was not apparent. In this exemplifying case, the conclusion is that the binding effect occurred at specific antibody concentration. For a virus-based suspension, embodiments therefore use a fixed antibody concentration and serially dilute the virus suspensions and conduct the binding measurements. At a specific virus concentration, binding effect will appear on the optical response.

FIGS. 6(*c*) and (*d*) illustrate the corresponding optical responses for, in this example, NC protein and its corresponding antibody when they were mixed either inside (FIG. 6(*c*)) or outside (FIG. 6(*d*)) the microcentrifuge tube, respectively. Peaks, or humps, in the light intensity indicating binding activities are marked with circles in the graphs. Inside mixing means that the protein was added to the tube and the antibody was added after 100 seconds, while in the outside mixing scenario, both the protein and antibody were mixed prior to being loaded in the tube for optical measurements. As can be seen, the binding response could be detected in each case in the form of the appearance of the hump. However, this "hump" was a lot more pronounced when the protein and the antibody were mixed prior to test testing than when they were added sequentially. When employing embodiments in real life scenarios with patient samples, the antibody should be already bound to the viral or bacterial antigen at the time of detection. Preferably a potentially virus containing sample from a patient should be mixed with antibody before optical detection measurement.

Figure 7A:
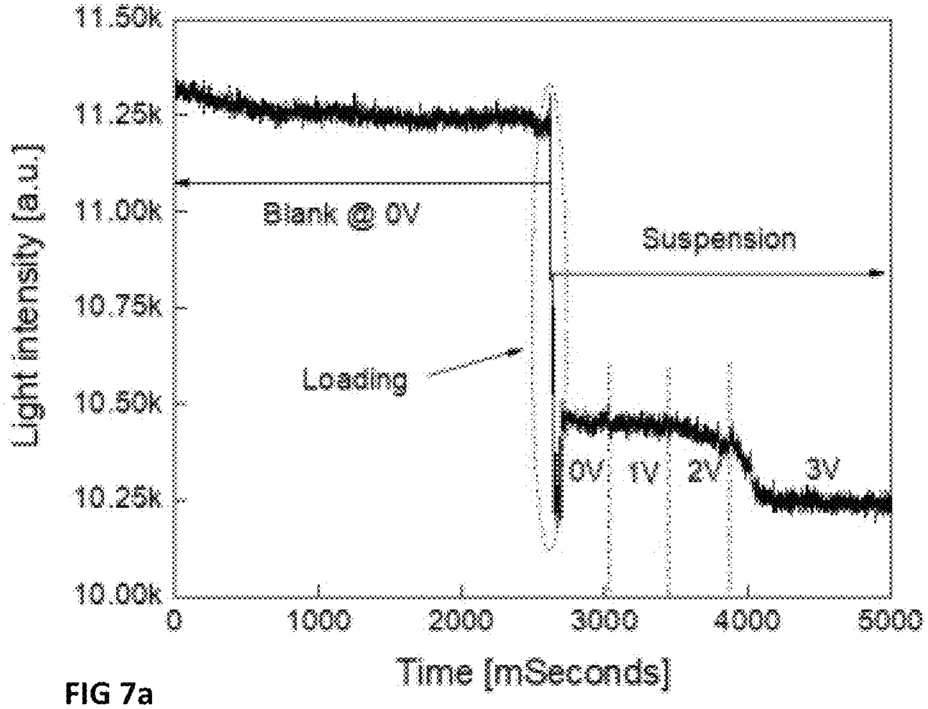
Figure 7B:
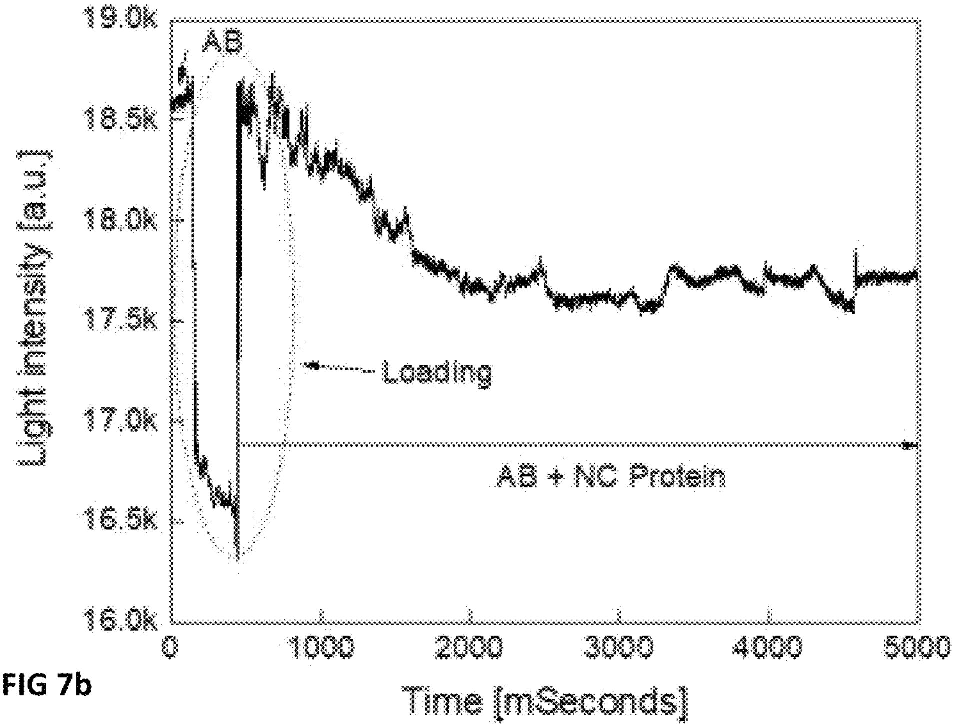

Embodiments makes use of the effect of direct current DC biasing on the ability of two proteins to bind specifically. An example to illustrate this was carried out by subjecting the nucleocapsid protein (NCP or NC protein) solution to DC voltage bias. FIG. 7 shows graphs of Opto-electrical measurements of nucleocapsid protein (NC protein) with direct current DC biasing. FIG. 7(*a*) shows an example of measured NC protein optical response versus time at different DC bias voltages. An applied bias should result in an induction of current across the suspension. If this current is high enough, it should have the potential to destroy the protein physiology and functionality, resulting in the loss of specific protein-protein interactions. In this example, the NC protein solution was loaded in an electroporation cuvette (rather than a microcentrifuge tube as in previous examples) that incorporates two electrodes with a volume of 0.5 mL and a separation distance of 0.4 cm. This should result in a breakdown electric field of 7.5 V/cm. At this field onwards, the binding between the protein and the antibody should be affected. Above this field the sample will be incapacitated. As shown in FIG. 7(*a*), the optical response decays slowly with the application of DC bias. At 3 volts DC bias, the optical response decays with a considerable step, and increasing the DC bias further should burn the suspension and destroy it.

The breakdown field depends on the electrical characteristics of both the buffer and the analyte such as proteins, viruses, etc. In further exemplifying application of embodiments, the suspension of protein was subjected to 3 V for 1 minute and then the antibody to nucleocapsid NC was added to the NC protein solution. The corresponding measured response is shown in FIG. 7(*b*). The measured response was observed to be noisy and did not show a clear binding effect when compared with FIG. 6(*c*) that shows the optical response for the same protein and antibody without the application of DC bias. Embodiments are configured to create a corresponding vaccine for a disease by subjecting its corresponding virus to DC bias which will affect its infectivity and destroy its physiology and communicability. Furthermore, embodiments of the optical detection in time domain are configured to be used for monitoring and detecting the efficiency of vaccine process development.

Figure 8A:
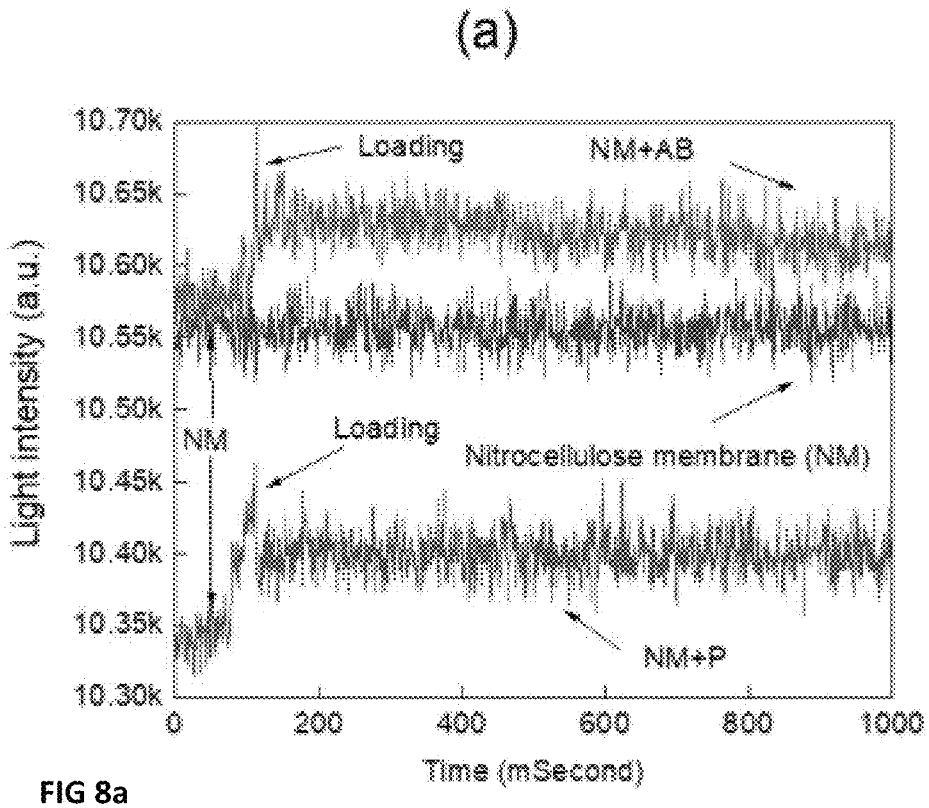
Figure 8B:
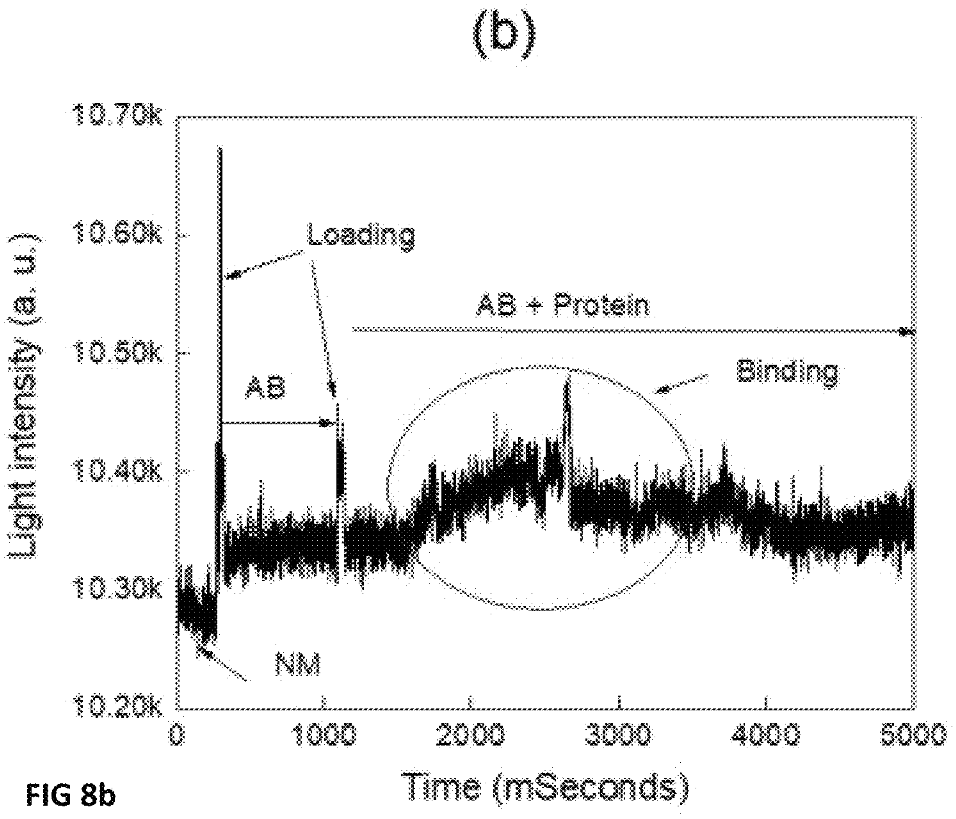

Embodiments are configured for virus detection on samples on paperbased nitrocellulose membrane. The nitrocellulose membrane is a popular matrix that is frequently used due to its high protein-binding affinity with a pore size of 0.25-0.45 μm in paper-based diagnostics. Protein molecules usually bind to the nitrocellulose membranes through hydrophobic interactions. Due to the ease of their handling, cheap cost, and the presence of hydrophobic interactions between them and the suspended proteins, we tested whether the binding between the SARS-CoV-2 spike protein and antibody could be detected optically when both were added to each other on the nitrocellulose membrane. Using embodiments illustrated with the experimental setup described in FIG. 2(*a*), the optical responses for nitrocellulose membrane, nitrocellulose membrane and spike protein alone, nitrocellulose membrane and antibody against spike protein alone, and nitrocellulose membrane spike protein-antibody were measured in illustrating example. FIG. 8 shows graphs of this illustrating example of protein-protein interaction measurements on paperbased nitrocellulose membrane (NM).

FIG. 8(*a*) shows optical responses on nitrocellulose membrane (NM) alone, nitrocellulose membrane and spike protein (NM+P), and nitrocellulose membrane and antibody to spike protein (NM+AB) alone. The graph in FIG. 8(*a*) shows that both the antibody alone and spike protein alone exhibited higher light intensity than the nitrocellulose membrane alone with almost a straight line with constant slope over a time period of 10 seconds. The on-paper measured optical responses exhibited fluctuations as in the samples measured using microcentrifuge tubes. This implies that these fluctuations are not due to any kind of interactions, but instead are due to the spectrometer conversion process. FIG. 8(*b*) summaries the interaction measurements which start with the membrane NM. After 100 mSecond, the antibody suspension AB was loaded on the membrane and measurements were conducted up to 1000 mSecond. Next, the spike protein sample was loaded AB+Protein and measurements were continued up to 5000 mSecond. As shown in FIG. 8(*b*), the interaction peaks appeared clearly within the indicating circle. It is worth noting that the membrane size, shape, and charge of biomolecules, pH and viscosity of the control buffer, as well as the composition influences the corresponding optical response and binding interactions.

Figure 9:
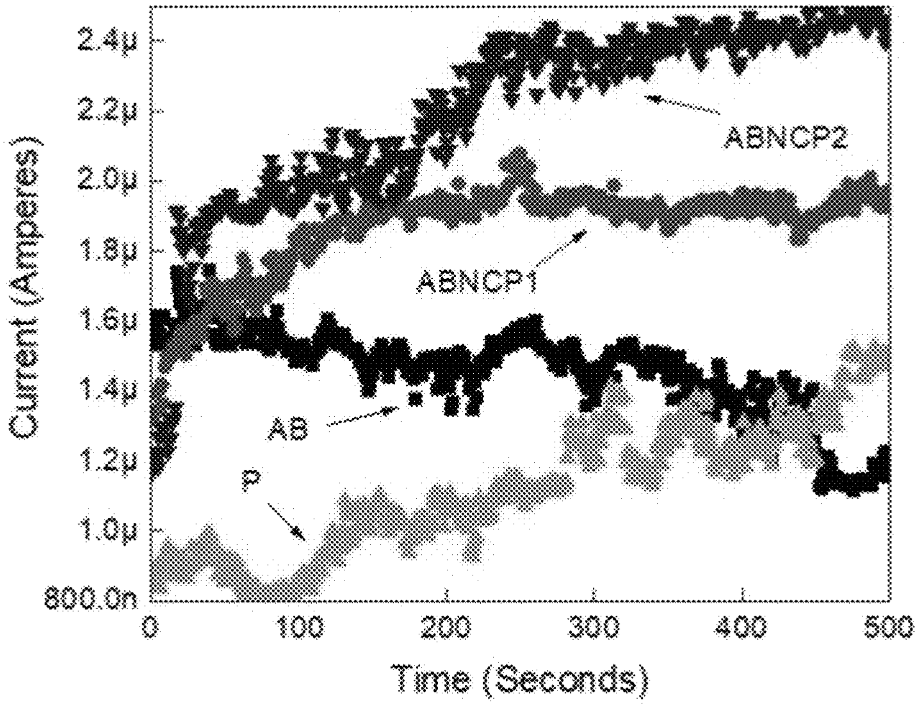
FIG. 9 shows a graph of chronoamperometry measurements indicating current versus time for different sample suspensions, in accordance with embodiments.

As these illustrating protein-antibody interactions took place within a time domain, the measurements are further illustrated using the well-known technique of chronoamperometry to detect this interaction electrically. Chronoamperometry is an electrochemical technique in which an electric potential is applied between two electrodes to measure the resulting current at the surface that is created from faradaic processes over time. The corresponding chronoamperometry measurements were conducted accordingly as plotted in FIG. 9. FIG. 9 thus shows a graph of chronoamperometry measurements indicating current versus time for different sample suspensions, in accordance with embodiments. In FIG. 9, the lowest curve shows protein P (NCP), the second lowest curve shows antibody AB, whereas the next to upper curve shows a first measurement on protein-antibody suspension ABNCP1 and the uppermost curve shows a second measurement on protein-antibody suspension ABNCP2. The two curves ABNCP1 and ABNCP2 pertain to two different measurements that uses the same nucleoprotein and the same antibody.

The applied potential in this example was of 0.5 mVolts, the minimum voltage that can be applied without causing any harm to the protein and antibody; therefore, it should not have affected the interaction process. As shown in FIG. 9, the electrical current measurements for the protein-antibody suspensions ABNCP1 and ABNCP2 exhibited exponential growth profiles, whereas the individual profiles for protein P (NCP) and antibody AB did not exhibit such behaviour. These embodiments can be used in a detection strategy. As shown in FIG. 9, the binding took place between 50 and 250 seconds, a period during which protein-antibody solutions ABNCP1 and ABNCP2 (ABP) exhibited higher measured electrical current values compared with protein P or antibody AB currents alone.

As described and illustrated in the above examples, different embodiments are configured as follows.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

What is claimed is:

1. A method of opto-electrical detection of the presence of bindings or interactions between analytes in a sample, comprising:

using a sample strip to collect analytes from a test subject, wherein the sample strip is coated with an antibody configured to bind or interact with a SARS-CoV-2 virus, resulting in the sample strip containing a sample containing analytes from the test subject and selected antibodies;

exposing the sample to light from a light source;

detecting light passing through the sample;

applying an electrical field over the sample in order to enhance the bindings or interactions between the analytes;

determining the values of a selection of light scattering parameters for the light passing through the sample in response to the electrical field; and/or determining the values of a selection of electrical scattering parameters in response to the electrical field;

determining the presence of bindings or interactions between analytes in the sample based on the values of the determined light scattering parameters and/or the determined values of the electrical scattering parameters used for SARS-CoV-2 virus detection and comprising collecting and processing electrical and optical responses individually or simultaneously to extract a set of parameters for detection, quantification, and identification of virus;

wherein a characteristic of the determined light scattering parameters, and/or electrical scattering parameters, for specific values of the electric parameters is determined to measure the viral nucleocapsid protein and anti-N antibody interactions in the sample to differentiate between SARS-CoV-2 negative and positive samples.

2. The method of claim 1, wherein the presence of bindings or interactions between analytes in the sample is determined based on a predetermined characteristic of the detected light scattering parameters, and/or electrical scattering parameters, for specific values of the electric parameters.

3. The method of claim 1, wherein a selection of one or more light scattering parameters and/or electrical scattering parameters are measured and possibly recorded over a time-period and/or mapped to a time domain.

4. The method of claim 1, wherein:

the sample is added to a holder or container aligned with the light source and the light detector such that measurement of light passing through the sample is enabled; and measured responses in the form of the determined values of said selection of optical or electrical parameters in response to the electrical field are collected to determine the presence of bindings or interactions between analytes in the sample.

5. The method of claim 4, wherein collecting measured responses comprises one or more of:

collecting directly measured light intensity; and/or collecting directly measured light intensity and establishing direct relationship with time; and/or processing direct measured data to extract parameters or a set of parameters and correlating said parameters with time to establish relationship with the presence of bindings or interactions between analytes in the sample.

6. The method of claim 1, wherein a mathematical relation for the determined parameters represents the process of bindings or interactions between analytes in the sample.

7. The method of claim 1, wherein the presence and/or the process of one or more of said bindings or interactions is determined, detected and/or monitored based on measurements of one or more of the voltage, the current, the capacitance and/or the impedance over time in relation to a said applied electric field.

8. The method of claim 1, further being adapted and used for detection of one or more of virus from the group MERS, influenza, respiratory syncytial virus (RSV), adenoviruses, or any other respiratory virus.

9. The method of claim 1, further comprising applying an electrical pulse over or through the sample, thereby enabling electro-insertion of said selected antibodies into any virus cell present in the sample.

10. The method of claim 1, wherein:

said sample is placed and distributed in one or more microfluidic channels;

measurement of said light scattering parameters and/or said electrical parameters is conducted for the sample content in each of said microfluidic channels; and virus concentration and/or virus load is determined based on said measured parameters.

11. The method of claim 10, wherein:

said sample is placed and distributed in a plurality of parallel microfluidic channels;

an antibody content is serially diluted in said plurality of parallel channels, simultaneously measuring said parameters in said plurality of channels; and said virus concentration and/or virus load is determined based on said measured parameters.

12. A system of opto-electrical detection of the presence of bindings or interactions between analytes in a sample, comprising:

using a sample strip to collect analytes from a test subject, wherein the sample strip is coated with an antibody configured to bind or interact with a SARS-CoV-2 virus, resulting in the sample strip containing a sample containing analytes from the test subject and selected antibodies;

a light source configured to emit or transfer natural or manmade light and to expose the sample with said light;

an electric field device configured to apply a biasing electric field over the sample to enhance the bindings or interactions between the analytes;

a light detector configured to detect light passing through a said light exposed sample;

an electric parameter detector configured to detect electric parameters;

a processing device having code portions configured to direct the processing device to:

determine the values of a selection of one or more light scattering parameters of the detected light passing through a said light exposed sample;

determine the values of a selection of electrical parameters in response to the electrical field, and to determine the presence of bindings or interactions between analytes in the sample based on the values of the determined light scattering parameters, and/or electric scattering parameters, and the determined values of the electrical parameters;

collect and process electrical and optical responses individually or simultaneously to extract a set of parameters for detection, quantification and identification of virus; and determine a characteristic of the light scattering parameters, and/or an electrical scattering parameter, for specific values of the electric parameters and to measure the viral nucleocapsid protein and anti-N antibody interactions in the sample to differentiate between SARS-CoV-2 negative and positive samples.

13. The system of claim 10, wherein the processing device comprises code portions configured to determine the presence of bindings or interactions between analytes in the sample based on a predetermined characteristic of the detected light scattering parameters, and/or detected electrical scattering parameters, for specific values of the electric parameters.

14. The system of claim 12, further comprising: a transparent holder or container allowing light to pass through the material without appreciable scattering of light and being configured for holding a sample.

15. The system of claim 12, wherein the electric field device comprises two electrodes configured or configurable at respective sides of a sample and being couplable to an electric energy source.

16. The system of claim 12, wherein the processing device comprises code portions configured to apply a mathematical relation for the determined parameters to represent the process of bindings or interactions between analytes in the sample.

17. The system of claim 12, wherein the processing device comprises code portions configured to determine, detect and/or monitor the presence and/or the process of one or more said bindings or interactions based on measurements of one or more of the voltage, the current, the capacitance and/or the impedance over time in relation to a said applied electric field.

18. The system of claim 12, further being adapted and used for detection of one or more of virus from the group SARS, MERS, influenza, respiratory syncytial virus (RSV), adenoviruses, or any other respiratory virus.

19. The system of claim 12, further being configured to apply an electrical pulse over or through a sample containing analytes from a test subject and selected antibodies, thereby enabling electro-insertion of said antibodies into any virus cell present in the sample.

20. The system of claim 12, wherein the sample strip includes an electrode coated thereon and configured to conduct current measurements directly, and wherein said sample strip includes a portion coated with antibodies.

21. The system of claim 20, wherein the sample strip is coated with an antibody configured to bind or interact with of one or more of virus from the group SARS, MERS, influenza, respiratory syncytial virus (RSV), adenoviruses, or other respiratory virus.

22. The system of claim 12, further comprising: a device for nasal sampling configured such that the sample strip is attachable at a section of the nasal sampling device that is configured to be insertable in the nose of a human test object, the nasal sampling device comprising two electrodes configured to apply an electric field over a sample of analytes collected on the sample strip.

23. The system of claim 12, wherein the nasal sampling device further comprises an integrated light source and detector configured to expose the sample to light and to detect light passing through the sample.

24. The system of claim 12, configured such that when the presence of a binding or interaction between a virus and an antibody is detected in a sample from a patient, an indication signal is presented confirming that patient is infected with the tested virus.

25. The system of claim 12, comprising:

a microfluidic sensing device with one or more one or more microfluidic channels configured for placing and distributing a said sample in one or more of said microfluidic channels;

one or more sensors configured for measurement of said light scattering parameters and/or said electrical parameters for the sample content in each of said microfluidic channels; and code portions, in said processing device, configured to determine virus concentration and/or virus load based on said measured parameters.

26. The system of claim 25, wherein:

said microfluidic sensing device is configured with a plurality of parallel microfluidic channels for placing and distributing said sample;

said microfluidic sensing device is configured for serially diluting an antibody content in said plurality of parallel channels, simultaneously measuring said parameters in said plurality of channels; and said system is configured to determine said virus concentration and/or virus load based on said measured parameters.

* * * * *